US008526573B2

(12) United States Patent
Ferro, Jr.

(10) Patent No.: US 8,526,573 B2
(45) Date of Patent: Sep. 3, 2013

(54) SYSTEMS AND METHODS FOR REMOTE DIAGNOSTIC IMAGING

(75) Inventor: Michael W. Ferro, Jr., Chicago, IL (US)

(73) Assignee: Merge Healthcare Incorporated, Chicago, IL (US)

( * ) Notice: Subject to any disclaimer, the term of this patent is extended or adjusted under 35 U.S.C. 154(b) by 118 days.

(21) Appl. No.: 12/953,137

(22) Filed: Nov. 23, 2010

(65) Prior Publication Data

US 2011/0122995 A1      May 26, 2011

Related U.S. Application Data

(60) Provisional application No. 61/264,365, filed on Nov. 25, 2009.

(51) Int. Cl.
*H05G 1/64* (2006.01)
(52) U.S. Cl.
USPC .............................. 378/98; 378/62
(58) Field of Classification Search
USPC .................. 378/98, 91, 98.2, 98.5, 98.8, 102, 378/114, 115, 62
See application file for complete search history.

(56) References Cited

U.S. PATENT DOCUMENTS

| | | |
|---|---|---|
| 3,783,251 A | 1/1974 | Pavkovich |
| 4,181,347 A | 1/1980 | Clark |
| 4,361,730 A | 11/1982 | Barber et al. |
| 4,425,978 A | 1/1984 | Star |
| 4,449,746 A | 5/1984 | Clark |
| 4,570,733 A | 2/1986 | Star |
| 4,644,705 A | 2/1987 | Saccomani et al. |
| 4,838,275 A | 6/1989 | Lee |
| 4,845,636 A | 7/1989 | Walker |
| 4,915,435 A | 4/1990 | Levine |
| 5,012,411 A | 4/1991 | Policastro et al. |

(Continued)

FOREIGN PATENT DOCUMENTS

| | | |
|---|---|---|
| JP | 2002112991 | 4/2002 |
| KR | 1019970071316 | 11/1997 |

OTHER PUBLICATIONS

PCT/US2010057855 International Search Report dated Jun. 21, 2011 (5 pages).

(Continued)

*Primary Examiner* — Hoon Song
(74) *Attorney, Agent, or Firm* — Michael Best & Friedrich LLP

(57) ABSTRACT

Systems and methods for remote diagnostic imaging. The systems include a diagnostic imaging kiosk. The kiosk includes, for example, a first housing module and a second housing module. The first housing module is configured to house, among other things, a diagnostic imaging system (e.g., an X-ray system). The second housing module is configured to house electronics associated with the operation, control, and networking of the kiosk. The electronics include, for example, a primary controller, an X-ray controller, an X-ray generator, an internal display controller, an external display controller, one or more routers, and a digital radiology module. The kiosk is configured to communicatively connect to a remote technician's workstation, and a remote technician at the workstation is able to remotely control the kiosk through a packet-switched network. The control of the kiosk includes controlling access to the kiosk, the position of a diagnostic imaging unit, the capture of diagnostic images, the display of information to a patient, etc.

10 Claims, 16 Drawing Sheets

(56) References Cited

U.S. PATENT DOCUMENTS

| | | | |
|---|---|---|---|
| 5,014,267 A | 5/1991 | Tompkins et al. | |
| 5,054,044 A | 10/1991 | Audon et al. | |
| 5,297,034 A | 3/1994 | Weinstein | |
| 5,343,240 A | 8/1994 | Yu | |
| 5,544,649 A | 8/1996 | David et al. | |
| 5,727,353 A | 3/1998 | Getz et al. | |
| 5,801,755 A | 9/1998 | Echerer | |
| 5,913,019 A | 6/1999 | Attenberg | |
| 6,022,315 A | 2/2000 | Iliff | |
| 6,046,761 A | 4/2000 | Echerer | |
| 6,179,358 B1 | 1/2001 | Hirayama et al. | |
| 6,206,829 B1 | 3/2001 | Iliff | |
| 6,353,445 B1 | 3/2002 | Babula et al. | |
| 6,369,847 B1 | 4/2002 | James et al. | |
| 6,403,897 B1 | 6/2002 | Bluth et al. | |
| 6,428,124 B1 | 8/2002 | Bluth et al. | |
| 6,445,185 B1 | 9/2002 | Damadian et al. | |
| 6,481,887 B1 | 11/2002 | Mirabella | |
| 6,482,156 B2 | 11/2002 | Iliff | |
| 6,485,415 B1 | 11/2002 | Uchiyama et al. | |
| 6,492,812 B1 | 12/2002 | Debbins et al. | |
| 6,511,435 B1 | 1/2003 | Bluth et al. | |
| 6,594,607 B2 | 7/2003 | Lavery | |
| 6,692,436 B1 | 2/2004 | Bluth et al. | |
| 6,849,045 B2 | 2/2005 | Iliff | |
| 6,999,558 B2* | 2/2006 | Okoda | 378/102 |
| 7,306,560 B2 | 12/2007 | Iliff | |
| 7,347,472 B2 | 3/2008 | Pellegrin, Jr. | |
| 7,384,146 B2 | 6/2008 | Covannon et al. | |
| 2003/0181804 A1 | 9/2003 | Gagnon et al. | |
| 2005/0075907 A1 | 4/2005 | Rao | |
| 2005/0111620 A1* | 5/2005 | Livermore et al. | 378/63 |
| 2005/0251006 A1 | 11/2005 | Dellis | |
| 2006/0047188 A1 | 3/2006 | Bohan | |
| 2006/0095297 A1 | 5/2006 | Virik | |
| 2006/0106646 A1 | 5/2006 | Squilla et al. | |
| 2006/0111620 A1 | 5/2006 | Squilla et al. | |
| 2007/0003115 A1 | 1/2007 | Patton et al. | |
| 2007/0073113 A1 | 3/2007 | Squilla et al. | |
| 2007/0129610 A1 | 6/2007 | Squilla | |
| 2007/0201103 A1 | 8/2007 | Morgan | |
| 2007/0211922 A1 | 9/2007 | Crowley et al. | |
| 2009/0144084 A1 | 6/2009 | Neumaier | |
| 2009/0185727 A1 | 7/2009 | Beckmann et al. | |
| 2009/0240115 A1 | 9/2009 | Bluth | |
| 2009/0240528 A1 | 9/2009 | Bluth | |
| 2010/0027752 A1* | 2/2010 | Matsumoto | 378/115 |

OTHER PUBLICATIONS

PCT/US2010057855 Written Opinion of the International Searching Authority dated Jun. 21, 2011 (4 pages).

New Models, Yu A. Veip, A. I. Mazurov, and A. V. Semenov, "KRT-Electron Remote Control X-Ray Diagnostic Systems," 2003, (3 pages).

Digital Radiology Innovations for NTP, CheckTB, "Innovative Chest X-ray solutions accelerating Tuberculosis case detection," 2007, (20 pages).

Olivia Greets, PR Newswire, "New Olivia Greet Patient Check-in Solution Streamlines Healthcare Operations," May 4, 2009, (3 pages).

Sedecal, Optima Millennium, "All Purpose Radiographic System," available at least as early as Feb. 25, 2011, (4 pages).

\* cited by examiner

SYSTEMS AND METHODS FOR REMOTE DIAGNOSTIC IMAGING

RELATED APPLICATIONS

This application claims the benefit of previously-filed, U.S. Provisional Patent Application No. 61/264,365, filed Nov. 25, 2009, the entire content of which is hereby incorporated by reference.

BACKGROUND

Embodiments of the present invention relate to diagnostic imaging.

Diagnostic imaging usually requires a patient to travel to a hospital or clinic that is staffed by trained radiological professionals. Trained radiological professionals are required to ensure that, when an X-ray is taken, the patient is not exposed to an unnecessary level of radiation. The patient must also be properly positioned with respect to the X-ray machine to ensure that the X-ray image corresponds to an area of interest on the patient's body.

SUMMARY

A significant limitation on the availability of diagnostic imaging may be the requirement of a trained professional to administer various diagnostic tests, such as electron microscopy, radiography (e.g., X-rays), magnetic resonance imaging ("MRI"), nuclear medicine, photoacoustic imaging, breast thermography, tomography, ultrasound, and the like. A diagnostic imaging kiosk or station which enables the remote deployment of diagnostic imaging equipment greatly increases the ability of medical professionals to diagnose and treat patients. For example, the kiosk can be deployed in locations which do not otherwise have access to the technology or the trained professionals required to perform the diagnostic tests identified above.

As such, the invention provides a modularly deployable diagnostic imaging kiosk that allows patients in impoverished, remote, or underdeveloped locations to receive professionally supervised diagnostic imaging procedures, and the kiosk can be shipped and assembled without requiring the aid of radiological experts. The kiosk includes a first housing module and a second housing module. The first housing module is configured to house, among other things, a diagnostic imaging system (e.g., an X-ray system). The second housing module is configured to house electronics associated with the operation, control, and networking of the kiosk. The electronics include, for example, a primary controller, an X-ray controller, an X-ray generator, an internal display controller, an external display controller, a router, and a digital radiology ("DR") module. The kiosk is divided into first and second housing modules to enhance the isolation between the diagnostic imaging system and the corresponding electronics. For example, the first housing module can be lead-lined or at least partially lead-lined to limit or prevent radiation from damaging or otherwise affecting the electronics. Additionally or alternatively, the kiosk is divided into a first housing module and a second housing module such that the second housing module can be used in an interchangeable manner with diagnostic imaging systems of different modalities. For example, the electronics necessary to implement a diagnostic imaging kiosk for capturing X-ray images are, in many ways, similar to the electronics necessary to implement a diagnostic imaging kiosk for capturing different types of diagnostic images. As such, the second housing module is configured for use in diagnostic imaging kiosks having a variety of modalities. Additionally or alternatively, the second housing module is configured to be used independently of the first housing module. For example, the second housing module can be configured as a standalone kiosk that allows patients to, among other things, access account information, view diagnostic images, pay for procedures, schedule appointments, and the like.

The diagnostic imaging kiosk is configured to be controlled remotely and without the need for a trained radiological professional on-site with the kiosk. For example, a radiological professional is able to remotely control, among other things, the position of an X-ray tube, the position of a Bucky unit, the exposure of the X-ray, at least one camera, and the display of captured X-rays. Thus, the diagnostic imaging kiosk is able to be controlled remotely by different technicians at different times, and each technician is able to control multiple kiosks.

In one embodiment, the invention provides a diagnostic imaging system that includes a remote diagnostic imaging station and a diagnostic imaging control station. The remote diagnostic imaging station includes a diagnostic imaging device, a communications interface, and a user interface. The remote diagnostic imaging station is configured to be connected to a packet-switched network. The diagnostic imaging control station is separate from the remote diagnostic imaging station, and is communicatively connected to the remote diagnostic imaging station through the packet-switched network. The diagnostic imaging control station is configured to generate a position control signal and transmit the position control signal through the packet-switched network to the remote diagnostic imaging station. The position control signal is associated with a physical position of at least a portion of the diagnostic imaging device. The diagnostic imaging control station is also configured to generate a diagnostic imaging capture signal that is operable to initiate the capture of a diagnostic image, transmit the diagnostic imaging capture signal through the packet-switched network to the remote diagnostic imaging station, and display the captured diagnostic image.

In another embodiment, the invention provides a diagnostic imaging station that includes a user interface, a diagnostic imaging device, and a communications interface. The user interface is configured to provide patient instructions related to a diagnostic imaging procedure, and the diagnostic imaging device is configured to capture a diagnostic image. The communications interface is configured to connect to a packet-switched network and receive a position control signal through the packet-switched network. The position control signal is associated with a physical position of at least a portion of the diagnostic imaging device. The communications interface is also configured to receive a diagnostic imaging capture signal through the packet-switched network. The diagnostic imaging capture signal is operable to initiate the capture of the diagnostic image, and the user interface is further configured to display the diagnostic image.

In another embodiment, the invention provides a method of performing a diagnostic imaging procedure. The method includes connecting to a remote diagnostic imaging station through a packet-switched network, generating a position control signal associated with a physical position of at least a portion of a diagnostic imaging device, and transmitting the position control signal through the packet-switched network to the remote diagnostic imaging station. The method also includes generating a diagnostic imaging capture signal operable to initiate the capture of a diagnostic image, transmitting the diagnostic imaging capture signal through the packet-switched network to the remote diagnostic imaging station, and displaying the captured diagnostic image at the diagnostic imaging control station.

In another embodiment, the invention provides a method of performing a diagnostic imaging procedure. The method includes connecting to a diagnostic imaging control station through a packet-switched network, providing patient instructions related to the diagnostic imaging procedure, receiving a position control signal through the packet-switched network associated with a physical position of at least a portion of a diagnostic imaging device, receiving a diagnostic imaging capture signal through the packet-switched network operable to initiate the capture of a diagnostic image, and displaying the captured diagnostic image.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Embodiments of the invention described herein relate to a remotely and modularly deployable diagnostic imaging station or kiosk. The kiosk is configured to provide patients in impoverished, remote, underdeveloped, and other locations with access to professionally supervised diagnostic imaging procedures. The kiosk is configured to be shipped and assembled without requiring the aid of on-site radiological experts. The kiosk includes, for example, a first housing module and a second housing module. The first housing module is configured to house, among other things, a diagnostic imaging system (e.g., an X-ray system). The second housing module is configured to house electronics associated with the operation, control, and networking of the kiosk. The kiosk is configured to connect to a remote diagnostic technician's workstation through one or more networks, and a remote diagnostic technician is able to remotely perform and control the diagnostic imaging procedures. The kiosk is also configured to connect to one or more local, regional, national, or international health information networks or databases where patient data and test results are capable of being stored and accessed. For example, by connecting to the health information networks or databases, the kiosk is able to authenticate the identity of a patient, validate the patient's use of the kiosk, and control payments for the diagnostic imaging procedures. The kiosk's connections to the health information networks or databases also enable medical information to be displayed and medical records to be updated and transmitted using various forms of media.

Figure 1:
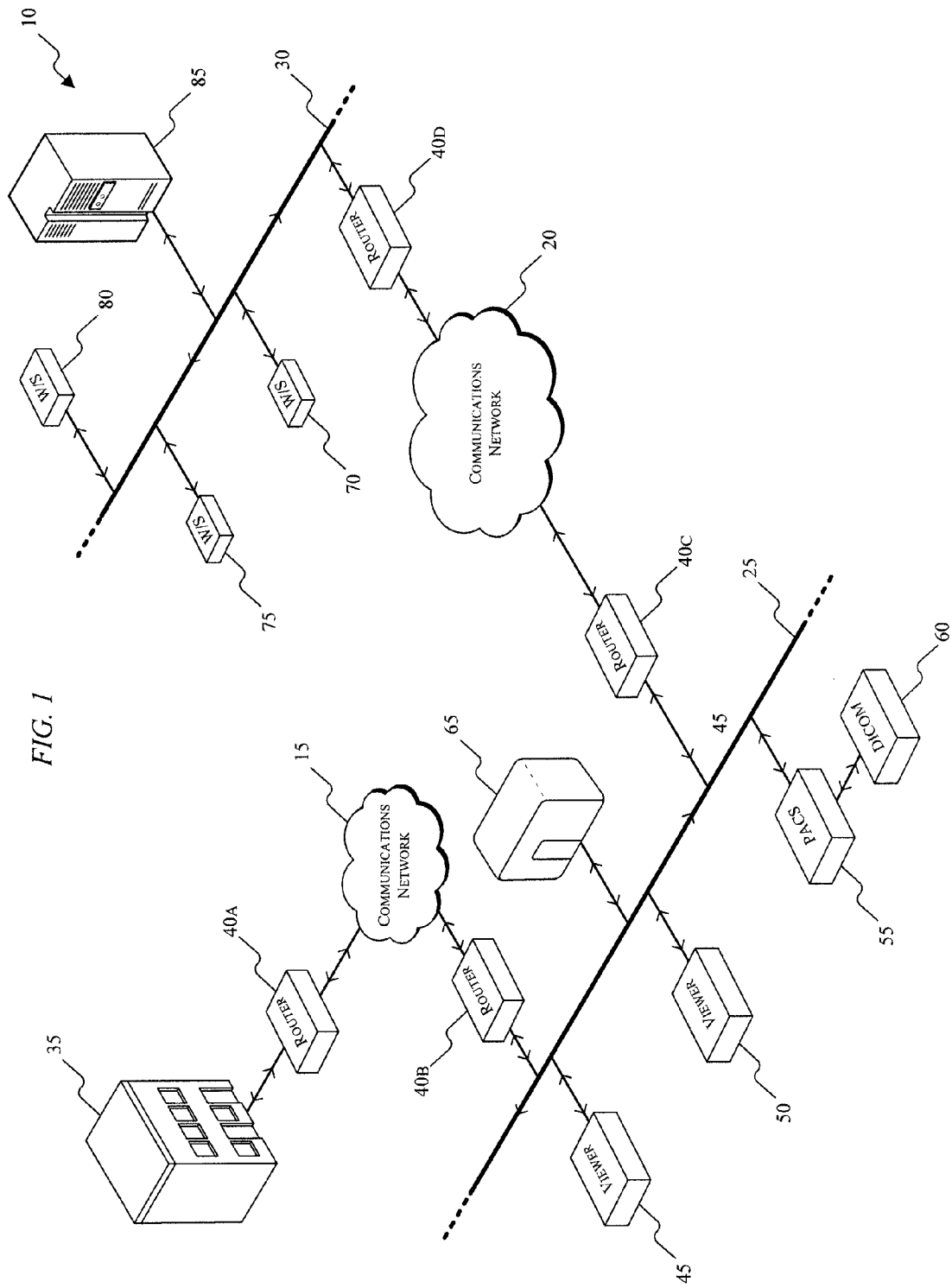
FIG. 1 illustrates a remote diagnostic imaging network according to an embodiment of the invention.

FIG. 1 illustrates a system 10 for implementing remote diagnostic imaging. The system 10 includes, among other things, a first communications network 15, a second communications network 20, a first local network 25, and a second local network 30. The first communications network 15, the second communications network 20, the first local network 25, and the second local network 30 are, for example, packet-switched networks. The first communications network 15 connects, for example, a hospital or other healthcare facility 35 to the first local network 25 via routers (e.g., fire-walled routers) 40A and 40B. The routers 40A and 40B, as well as routers 40C and 40D, are configured to connect to and provide communications through, for example, the first and second communications networks 15 and 20. In the illustrated embodiment, the healthcare facility 35 is connected to the first local network 25 via the first communications network 15. Also connected to the first local network 25 are a first viewing workstation 45 (e.g., an eFilm workstation), a second viewing workstation 50, a radiology information system ("RIS") picture archiving and communication system ("PACS") 55, a digital imaging and communications in medicine ("DICOM") database or storage area 60 (e.g., through the PACS), and a diagnostic imaging station or kiosk 65. Although only one diagnostic imaging kiosk 65 is illustrated, the system is configured to be used with a plurality of diagnostic imaging kiosks that can connect to the networks 15, 20, 25, and 30 or one or more additional or different networks. Additionally, although not illustrated in FIG. 1, the system 10 can also include additional routers for connecting the first viewing workstation 45, the second viewing workstation 50, the PACS 55, the kiosk 65, and the like to the first local network 25. For example, as described below, the kiosk 65 includes an internal bus or network. The internal network can be a part of the first local network 25, or can be connected to the first local network 25 via a router. Similarly, the kiosk 65 also includes an internal PACS which can be separate from the PACS 55 that is connected to the first local network 25.

The second communications network 20 is also connected to the first local network 25 via the router 40C and the second local network 30 via the router 40D. Also connected to the second local network 30 are a first technician workstation 70, a second technician workstation 75, a third technician workstation 80, and a server 85. The technician workstations 70, 75, and 80 and the server 85 are, for example, included in a datacenter which provides storage or access to diagnostic images, results, patient information, patient records, and the like.

In some embodiments, the first local network 25 and the second local network 30 are wired or wireless networks, such as, for example, a local area network ("LAN"), a neighborhood area network ("NAN"), a home area network ("HAN"), or personal area network ("PAN"), and use any of a variety of communications protocols (e.g., packet-switched), such as Wi-Fi, Bluetooth, ZigBee, or the like. The first communications network 15 and the second communications network 20 can be, for example, a wide area network ("WAN") (e.g., a TCP/IP based network, Global System for Mobile Communications ("GSM"), General Packet Radio Service ("GPRS"), Code Division Multiple Access ("CDMA"), Evolution-Data Optimized ("EV-DO"), Enhanced Data Rates for GSM Evolution ("EDGE"), 3GSM, Digital Enhanced Cordless Telecommunications ("DECT"), Digital AMPS ("IS-136/TDMA"), or Integrated Digital Enhanced Network ("iDEN"), a Digital Advanced Mobile Phone System ("D-AMPS"), or the like). In other embodiments, the first communications network 15 and the second communication network 20 can be a second LAN, HAN, or PAN. The connections between the various networks, components, devices, and buildings illustrated in FIG. 1 are, for example, wired connections, wireless connections, or a combination of wireless and wired connections.

In the illustrated embodiment, the networks and the communications between the devices within the networks are protected using one or more encryption techniques, such as those techniques provided in the IEEE 802.1X standard for port-based network security, pre-shared key ("PSK"), Extensible Authentication Protocol ("EAP"), Wired Equivalency Privacy ("WEP"), Temporal Key Integrity Protocol ("TKIP"), Wi-Fi Protected Access ("WPA"), or the like.

In some embodiments, alternative communications networks are used to communicate throughout the system 10. The alternative communications networks are, for example, a cellular network, such as a Global System for Mobile Communications ("GSM") network, a General Packet Radio Service ("GPRS") network, a Code Division Multiple Access ("CDMA") network, an Evolution-Data Optimized ("EV-DO") network, an Enhanced Data Rates for GSM Evolution ("EDGE") network, a 3GSM network, a 4GSM network, a Digital Enhanced Cordless Telecommunications ("DECT") network, a Digital AMPS ("IS-136/TDMA") network, or an Integrated Digital Enhanced Network ("iDEN") network. For example, in some embodiments, the kiosk 65 connects to a mobile switching center ("MSC"). The MSC allows the kiosk 65 to connect to a public switched telephone network ("PSTN") to communicate with the other parts of the system 10. In other embodiments, the alternative communications network is a satellite communications network. In such embodiments, the kiosk 65 connects to a constellation of satellites in, for example, geosynchronous orbit. The satellites forward messages from the kiosk 65 through a satellite teleport or ground station to the PSTN. Embodiments of the invention herein are described with respect to the first local network 25 and the second local network 30 being LANs, and the first communications network 15 and the second communications network 20 being WANs (e.g., the Internet) that use one or more TCP/IP based communications protocols, such as IPv4, IPv6, or the like. In other embodiments, the first communications network 15 is a different type of network than the second communications network 29, and/or the first local network 25 is a different type of network than the second local network 30.

Figure 2:
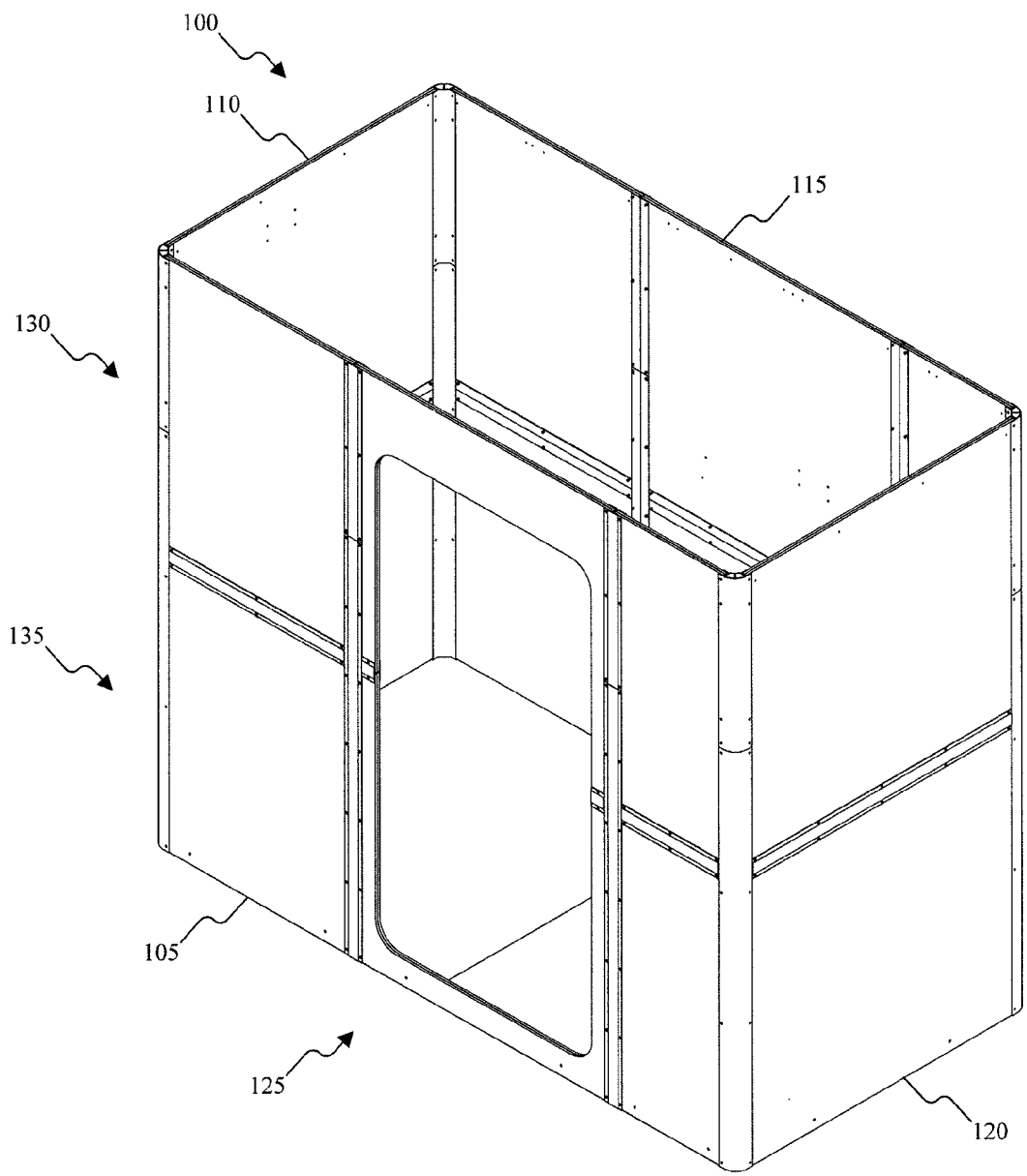
FIG. 2 illustrates a first diagnostic imaging kiosk module according to an embodiment of the invention.

FIG. 2 illustrates a first housing module 100 for the kiosk 65. In the illustrated embodiment, the first housing module 100 is rectangularly shaped and includes a first housing wall 105, a second housing wall 110, a third housing wall 115, and a fourth housing wall 120. The first housing wall 105 and the third housing wall 115 have a greater external surface area than the second housing wall 110 and the fourth housing wall 120. At least one of the first, second, third, and fourth housing walls 105-120 includes a lead lining to reduce or eliminate the transmission of radiation outside of the kiosk 65. In some embodiments, each of the first, second, third, and fourth housing walls 105-120 includes a lead lining. A doorway 125 is positioned approximately centrally on the first housing wall 105 to allow a patient to enter and exit the kiosk 65. The doorway 125 is configured to receive a door that secures the kiosk 65 and ensures privacy for patients within the kiosk 65. The door is, for example, a hinged door, a sliding door, or the like. To ensure the security and privacy of the kiosk 65, the door includes one or more electromagnetic locks for securely closing the door during a procedure or when the kiosk 65 is not in use. Although not illustrated in FIG. 2, the first housing module 100 also includes one or more speakers and one or more lights which are also configured to be remotely controlled by a remote technician.

In the illustrated embodiment of the kiosk 65, the first housing module 100, and particularly the first, second, third, and fourth housing walls 105-120, are divided into a top portion 130 and a bottom portion 135. The top and bottom portions 130 and 135 of each of the first, second, third, and fourth housing walls 105-120 allow the kiosk 65 to be transported in a smaller form factor, which reduces the costs associated with moving or transporting the kiosk 65, and does not significantly increase the complexity of assembling the kiosk 65. The first housing module 100 is constructed primarily of materials such as wood, metal, or a composite material.

Figures 3A, 3B:
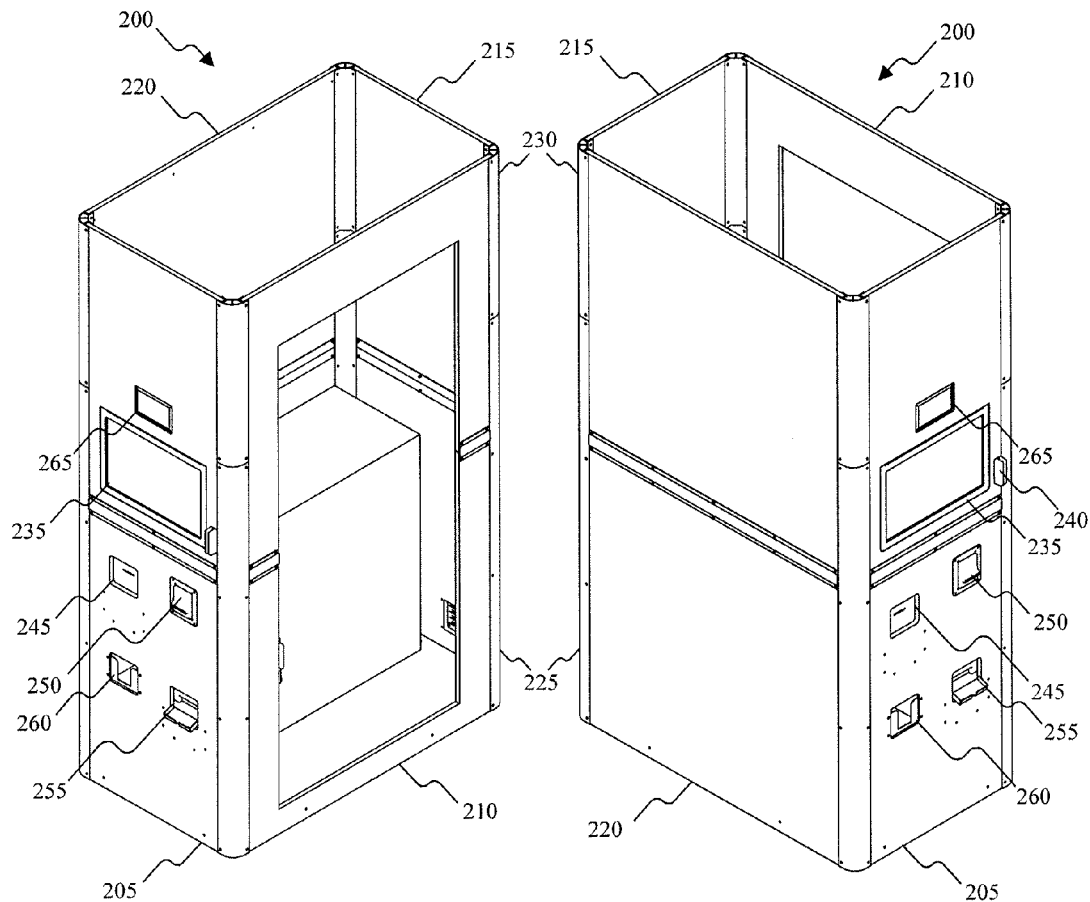
FIGS. 3A and 3B illustrate a second diagnostic imaging kiosk module according to an embodiment of the invention.

FIGS. 3A and 3B illustrate a second housing module 200. In a manner similar to the first housing module 100, the second housing module 200 is rectangularly shaped and includes a first housing wall 205, a second housing wall 210, a third housing wall 215, and a fourth housing wall 220. The second housing module 200 is also constructed primarily of materials such as wood, metal, or a composite material. Each of the first, second, third, and fourth housing walls 205-220 are also divided into bottom and top portions 225 and 230. As described above with respect to the first housing module 100, dividing the second housing module 200 into bottom and top portions 225 and 230 simplifies the transport of the kiosk 65 without significantly complicating assembly. The second housing module 200 also includes a doorway on the second housing wall 210. The doorway receives, for example, a hinged door that is capable of being locked (e.g., using an electromagnetic lock) to secure the contents of the second housing module 200. The contents of the second housing module 200 include, for example, computer hardware and other equipment, such as various control PCs, a magnetic card reader, an external (to the kiosk 65) touch screen display, external (to the kiosk 65) speakers, an X-ray generator, an X-ray control PC, communications equipment (e.g., for connecting to a network), and various other electronics used by the kiosk 65. The second housing module 200 also includes a plurality of apertures on the first housing wall 205 configured to receive or accommodate components of the second housing module such as, for example, the display 235, the magnetic stripe reader 240, the user identification card dispenser 245, the bill pay unit 250, the CD dispenser 255, and the CD cover holder 260. In other embodiments, the second housing module 200 also includes a scanner for scanning checks (e.g., personal checks). The scanned checks can then be processed for the payment of services and procedures.

In some embodiments, if the kiosk 65 includes the first housing module 100 and the second housing module 200, the kiosk is approximately eleven feet wide, nine feet tall, and between four and five feet wide. The specific dimensions depend on, for example, the diagnostic equipment included in the kiosk 65. The kiosk 65 can also be made smaller as advances in technology enable medical and communications equipment to be made smaller and more efficient.

Figure 4:
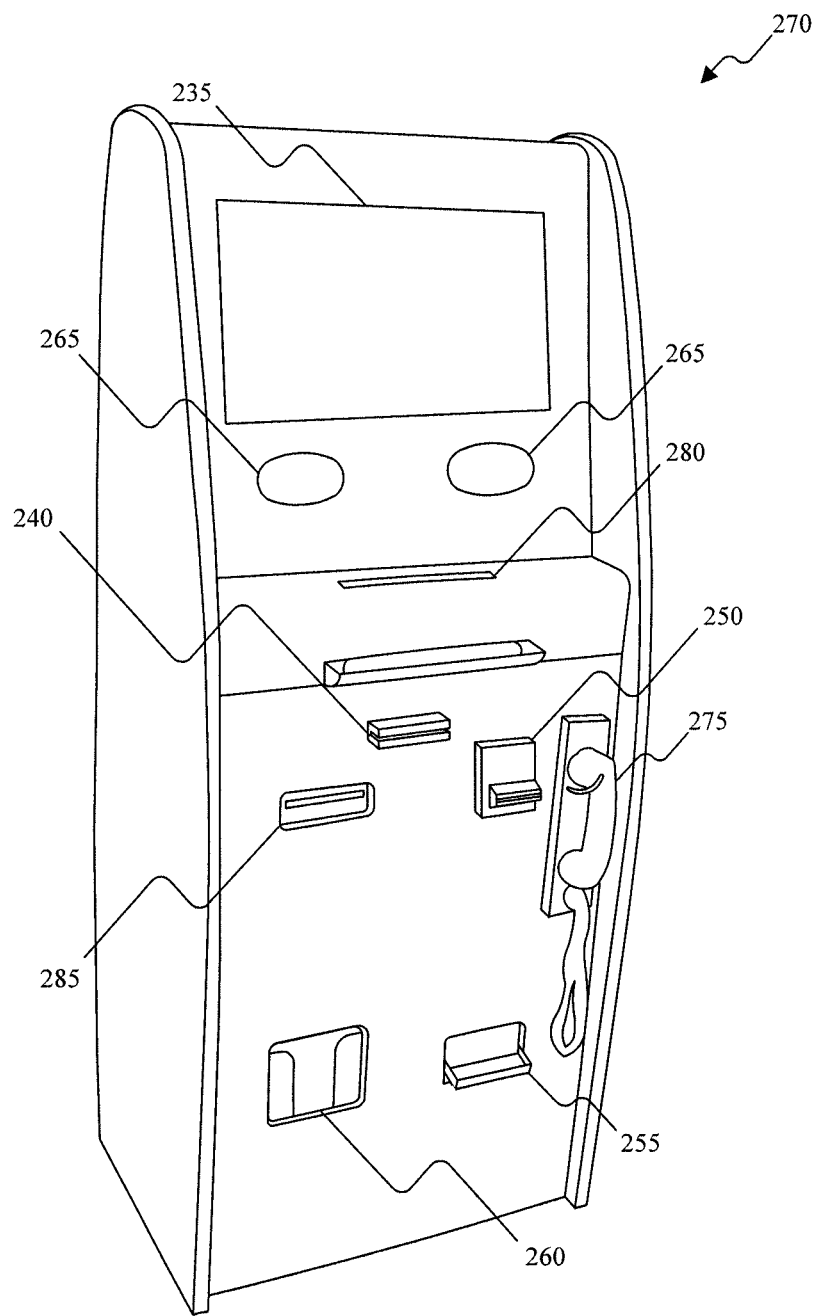
FIG. 4 illustrates a second diagnostic imaging kiosk module according to another embodiment of the invention.

FIG. 4 illustrates a second housing module 270 that is similar to the second housing module 200 described above. For example, the second housing module 270 includes a plurality of apertures configured to receive or accommodate components of the second housing module 270 such as, for example, the display 235, the magnetic stripe reader 240, the bill pay unit 250, the CD dispenser 255, and the CD cover holder 260. The second housing module 270 also includes a phone 275, a scanner 280, and a receipt dispenser 285. The scanner 280 is configured to scan items such as checks or user identification cards. The scanned items can then be processed for the payment of services and procedures or for the identification of the patient. The phone 275 is provided and configured to ensure the privacy of the patient when interacting with, for example, a remote technician or an assistance professional, as described below. In some embodiments, the second housing module 270 also includes the user identification card dispenser 245. The second housing module 270 is configured to be used independently of the first housing module 100. For example, the second housing module 270 is configured as a standalone kiosk that allows patients to, among other things, access account information, view diagnostic images, pay for procedures, schedule appointments, speak with remote technicians or assistance professionals, and the like.

Figure 5:
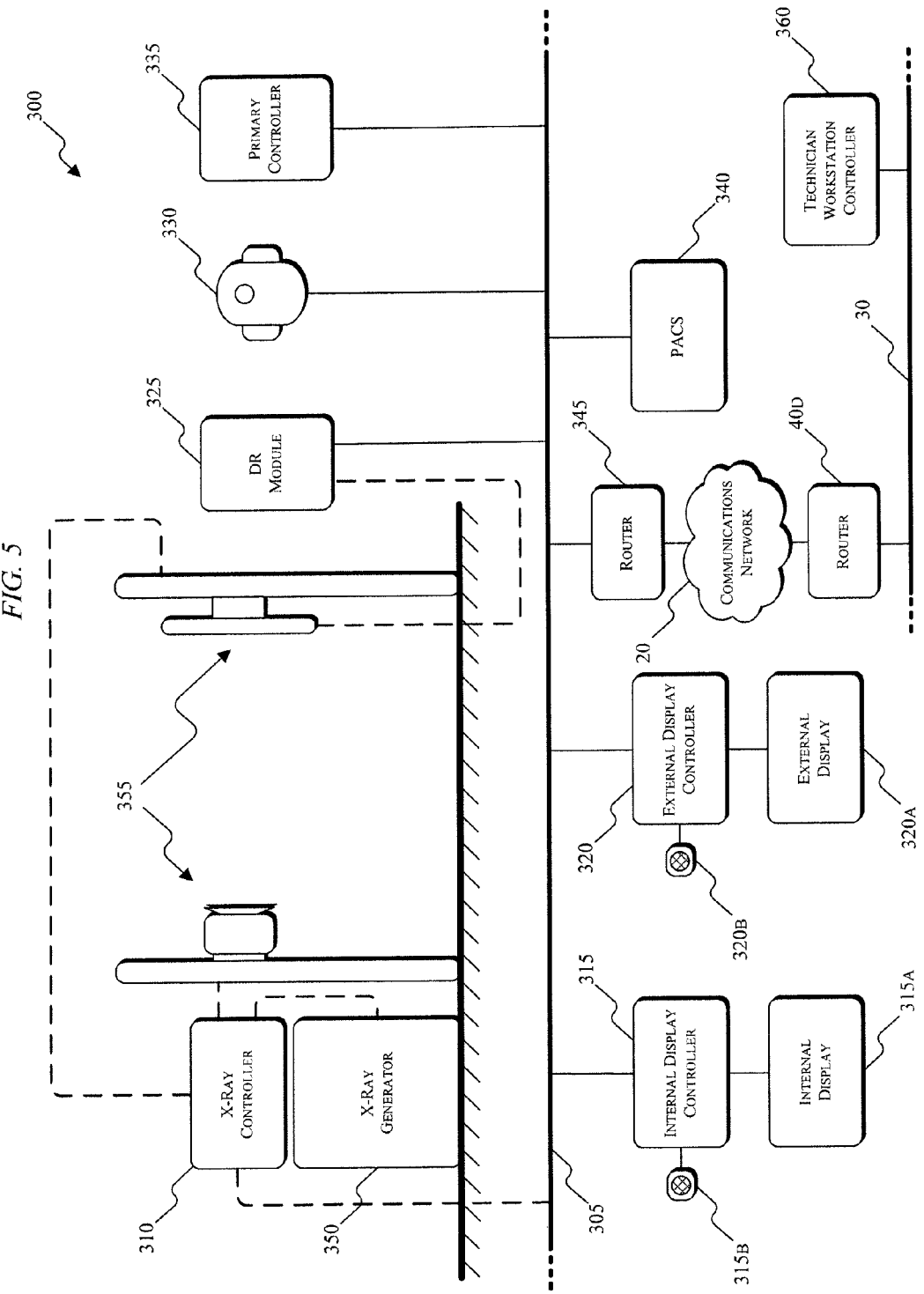
FIG. 5 illustrates local area network ("LAN") connections associated with a diagnostic imaging kiosk.

FIG. 5 illustrates the various interconnections between components within the kiosk 65 and the networks to which the kiosk 65 is connected. The electrical and electronic components within the kiosk 65 are generally connected to a bus, a LAN, or another suitable control and communication network within the kiosk 65. In the illustrated embodiment, the kiosk includes an internal LAN 305. The LAN 305 is configured to, for example, directly connect to the first local network 25 illustrated in FIG. 1, or connect to the first communications network 15 or second communications network 20 via one or more routers. In the illustrated embodiment, an X-ray controller 310, an internal touch screen display controller 315, an external touch screen display controller 320, a digital radiography ("DR") module or device 325, a surveillance device or camera 330 (e.g., a device capable of generating audio and video surveillance signals), a primary controller 335, a PACS 340, and a router 345 are connected to the LAN 305 of the kiosk 65. Other components within the kiosk 65, such as the X-ray generator 350 (e.g., a 64 kW, 150 kV, 400 mA generator), the X-ray device 355, the internal display or user interface 315A, the internal speaker 315B, the external display or user interface 320A, and the external speaker 320B, are connected to the LAN 305 through other components (e.g., the X-ray controller 310). The displays 315A and 320A are configured to, among other things, display information, instructions, advertisements, and the like to patients. In some embodiments, the kiosk 65 also includes one or more biometric screening devices (e.g., retinal scanners, finger print scanners, etc.) for verifying a patient's identify. A variety of security features can also be included in the kiosk 65. For example, the kiosk 65 includes one or more motion detectors, one or more alarms, one or more embedded global positioning devices (e.g., for locating the kiosk 65 or components within the kiosk 65), and the like.

The kiosk 65 is connected to the second communications network 20 via the router 345. A remote technician workstation controller 360 is connected to the second communications network 20 via the second local network 30 and the router 40D to enable a diagnostic imaging technician to remotely control the X-ray device 355, the camera 330, etc. The router 345 is also used to transmit diagnostic information and images to and from the kiosk 65. The PACS 340 is on-board or internal to the kiosk 65 and is configured to store, for example, full-resolution diagnostic images within the kiosk 65. Due to bandwidth limitations and the size of digital diagnostic imaging files, lower-resolution images are able to be presented to the remote technician and displayed on the internal display 315A. The full-resolution diagnostic images are stored locally in the kiosk 65's PACS 340 until, for example, off-peak bandwidth times (e.g., at night). At such times, the PACS 340 is configured to transfer the full-resolution diagnostic image to a networked database (e.g., the PACS 55 of FIG. 1).

Many of the components within the kiosk 65 are configured to operate independently of one another. For example, each of the controllers or devices within the kiosk 65 can include, among other things, a control unit, a user interface, and a display. The control unit includes, for example, a control or processing unit, a memory, an input/output ("I/O") module, a power supply module, and one or more busses for operably and communicatively coupling the components within the controller. The processing unit is, for example, a processor, a microprocessor, a microcontroller, or the like. The memory is a read-only memory ("ROM"), a random access memory ("RAM"), an electrically erasable programmable read-only memory ("EEPROM"), a flash memory, a hard disk, or another suitable magnetic, optical, physical, or electronic memory device. The I/O module includes, for example, routines for sending information to and receiving information from components or devices external to the controllers and for transferring information between components within the controllers. Software included in the components is stored in the memory. The software includes, for example, firmware applications and other executable instructions. In other embodiments, the controllers can include additional, fewer, or different components.

In some embodiments, the processing unit, the memory, and the I/O module of the controllers or devices are implemented on one or more printed circuit boards ("PCBs") within the components. For example, the PCB is populated with a plurality of electrical and electronic components which provide operational control and protection to the components. The PCB also includes, among other things, a plurality of additional passive and active components such as resistors, capacitors, inductors, integrated circuits, and amplifiers. These components are arranged and connected to provide a plurality of electrical functions to the PCB including, among other things, filtering, signal conditioning, and voltage regulation. For descriptive purposes, the PCB and the electrical components populated on the PCB are collectively referred to as controllers.

The kiosk 65 is powered by one or more power sources, such as an internal generator (e.g., a gasoline generator), mains power, solar panels, batteries, a battery pack, or a combination of such power sources. The kiosk 65 also includes, for example, an uninterruptible power supply ("UPS") that is configured to prevent the kiosk 65, and particularly core systems (e.g., controllers), within the kiosk 65 from losing power due to fluctuations in grid power, loss of grid power, or the like. For example, grid power is used to charge batteries and is not used to directly power components within the kiosk 65. In embodiments of the invention which include batteries, the batteries are alkaline-based or lithium-based batteries and are, for example, disposable or rechargeable AA batteries, AAA batteries, six-volt ("6V") batteries, nine-volt ("9V") batteries, or the like. In other embodiments, the components include a battery pack having a plurality of battery cells. The battery cells within the battery pack provide operational power (e.g., DC power) to the components. In one embodiment, each battery cell has a nominal voltage of approximately two-volts ("2.0V"), three-volts ("3.0V"), four-volts ("4.0V"), etc. The cells are arranged in series, parallel, or a series-parallel combination to achieve a desired nominal voltage for the battery pack. The battery cells are, for example, lithium-ion battery cells having a lithium-cobalt ("Li—Co"), lithium-manganese ("Li—Mn"), or Li—Mn spinel chemistry. In some embodiments, the battery cells have other suitable lithium or lithium-based chemistries. In other embodiments, the battery cells have a nickel-cadmium ("NiCd") chemistry, a nickel-metal hydride ("NiMH") chemistry, or another suitable nickel-based chemistry.

The display is configured to display a variety of information to the user. The user interface includes, for example, a keyboard, a touch-screen interface (e.g., a capacitive touch-screen interface), one or more physical buttons, switches, levers, sliders, or sensors (e.g., optical sensors), a voice-recognition system, a biometric screening system, a trackball, or the like. In some embodiments, each of the controllers includes a display. In other embodiments, internal and external displays 315A and 320A of the kiosk 65 are used to display information to the user. Additionally, the internal and external displays 315A and 320A can also be the user interfaces (e.g., touch-screen displays).

The I/O module includes, for example, a USB port, an SD card slot, a FireWire port, etc. The I/O module is used to connect the kiosk 65 to portable storage and processing devices (e.g., laptops, tablets, smartphones, etc.). Information stored within the kiosk 65 can be transferred to such devices, and allows the information stored within the kiosk 65 to be automatically or manually updated or backed-up. In some embodiments, diagnostic images can be transferred to a patient's mass storage device (e.g., a USB mass storage device) via the I/O module. Such a feature can be used in place of a printed CD.

The kiosk 65 is configured to receive payment from a variety of sources. For example, the kiosk 65 is configured to accept payment from a user via credit card, a web-based pay service, cash, check, or a prepaid service. As described above, the kiosk 65 includes a magnetic stripe reader 240 which allows a patient to pay for a service or procedure using a credit card, a debit card, a pre-paid credit card, or the like.

Figure 6:
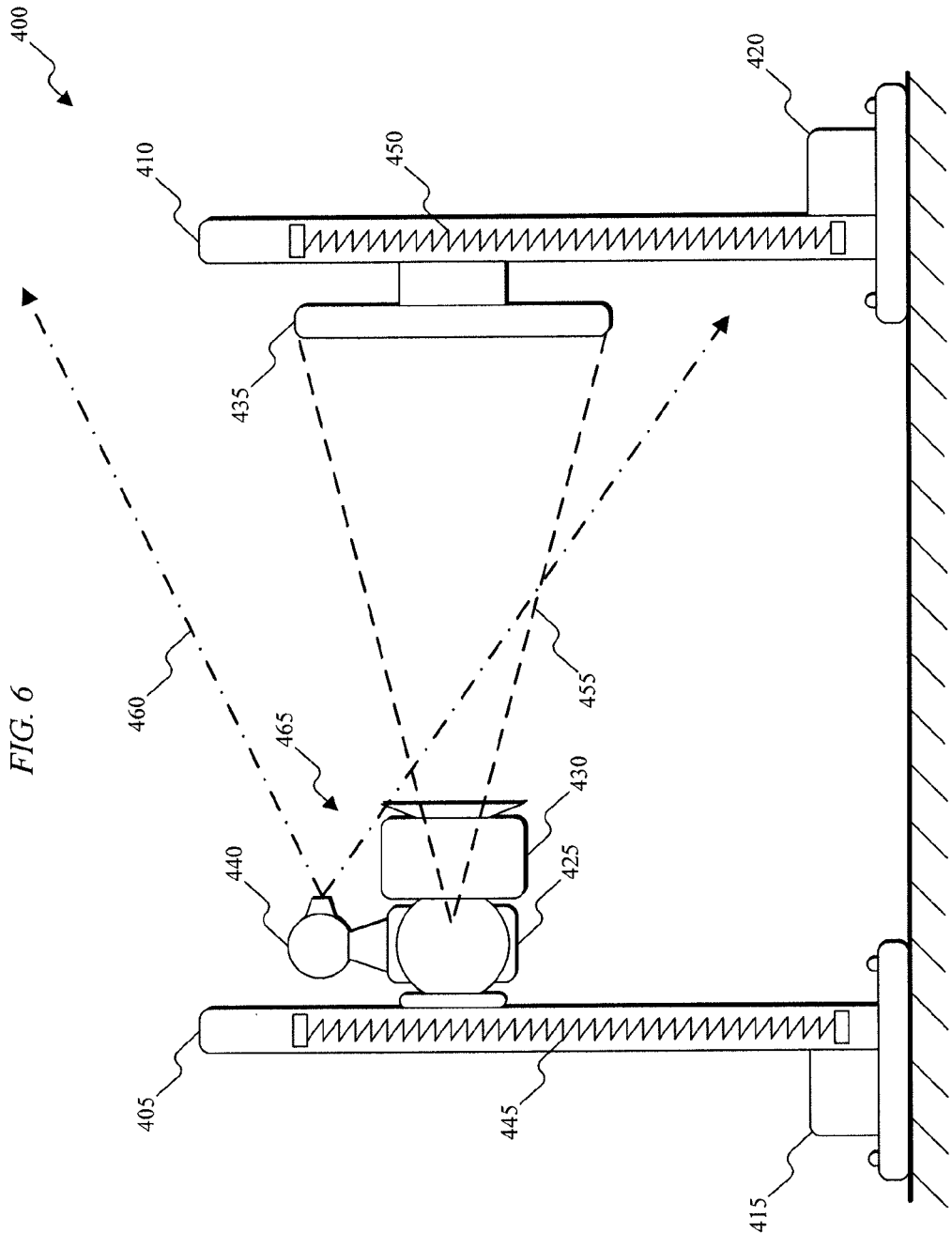
FIG. 6 illustrates a diagnostic imaging system for use in a diagnostic imaging kiosk.

FIG. 6 illustrates a diagnostic imaging system 400. In the illustrated embodiment, the diagnostic imaging system 400 is an X-ray system. The system 400 includes a first mounting portion or tube stand 405, a second mounting portion or tube stand 410, a first motor 415, a second motor 420, an X-ray source 425, an X-ray tube 430, a digital radiography ("DR") panel 435, a first networked video camera 440, a first positioning device 445, and a second positioning device 450. The X-ray source 425 and X-ray tube 430 have a first field-of-view ("FOV") 455, and the camera 440 has a second FOV 460. The X-ray source 425 and the X-ray tube 430 are collectively referred to herein as the X-ray unit 465. The first FOV 455 is adjusted using a collimator (not shown), and is adjusted remotely by a remote technician.

The X-ray unit 465 and the DR panel 435 are each controlled by a remote technician. For example, the X-ray unit 465 is connected to the first positioning device 445. The first positioning device 445 is connected to the first motor 415. The first motor 415 is configured to adjust the positioning of the X-ray unit 465 via the first positioning device 445 and based on one or more positioning signals received from the remote technician. Similarly, the second positioning device 450 is connected to the second motor 420. The second motor 420 is configured to adjust the positioning of the DR panel 435 via the second positioning device 450 and based on one or more positioning signals received from the remote technician. In some embodiments, the positions of the X-ray unit 465 and the DR panel 435 are synchronized such that the radiological technician is capable of raising or lowering the X-ray unit 465 and the DR panel 435 in synchronicity using one or more commands (e.g., a single raise or lower signal raises or lowers both the X-ray unit 465 and the DR panel 435). In some embodiments, the linear range of movement of the X-ray unit 465 and the DR panel 435 is approximately 150 cm. The positions of the X-ray unit 465 and the DR panel 435, as well as a height and a width of the collimator, are controlled, for example, over a control area network ("CAN") bus using a corresponding CAN communications protocol and based on the signals received from the remote technician. In some embodiments, the signals from the remote technician are processed and transmitted over the CAN bus by, for example, the X-ray controller 310 or the primary controller 335 shown in and described with respect to FIG. 5.

In the illustrated embodiment, the camera 440 is positioned above the X-ray unit 365 to provide the remote technician with a frontal video of the patient with respect to the DR panel 435. The camera 440 allows the remote technician to ensure that the patient is properly positioned with respect to the X-ray unit 465. In some embodiments, the X-ray unit 465 projects one or more lasers or light areas toward the DR panel 435 to assist in properly aligning the patient. The camera 440 also allows the remote technician to verify that necessary safety precautions (e.g., removing jewelry, etc.) have been satisfied. The second FOV 460 for the camera 440 is illustrated as being larger than the first FOV 455 for the X-ray unit 465 (e.g., the first FOV 455 of the X-ray unit 465 is within the second FOV 460 of the camera 440).

Although not illustrated in FIG. 6, some embodiments of the invention also include a laser distancing device for determining the distance between the patient and the X-ray unit 465 (e.g., to assist in determining a correct exposure), as well as a scale for determining an actual weight of the patient. In other embodiments, additional diagnostic devices or equipment can be included in the kiosk 65 to enable the testing of blood pressure, blood glucose, body fat, cholesterol, temperature, pulse, and the like.

Figure 7:
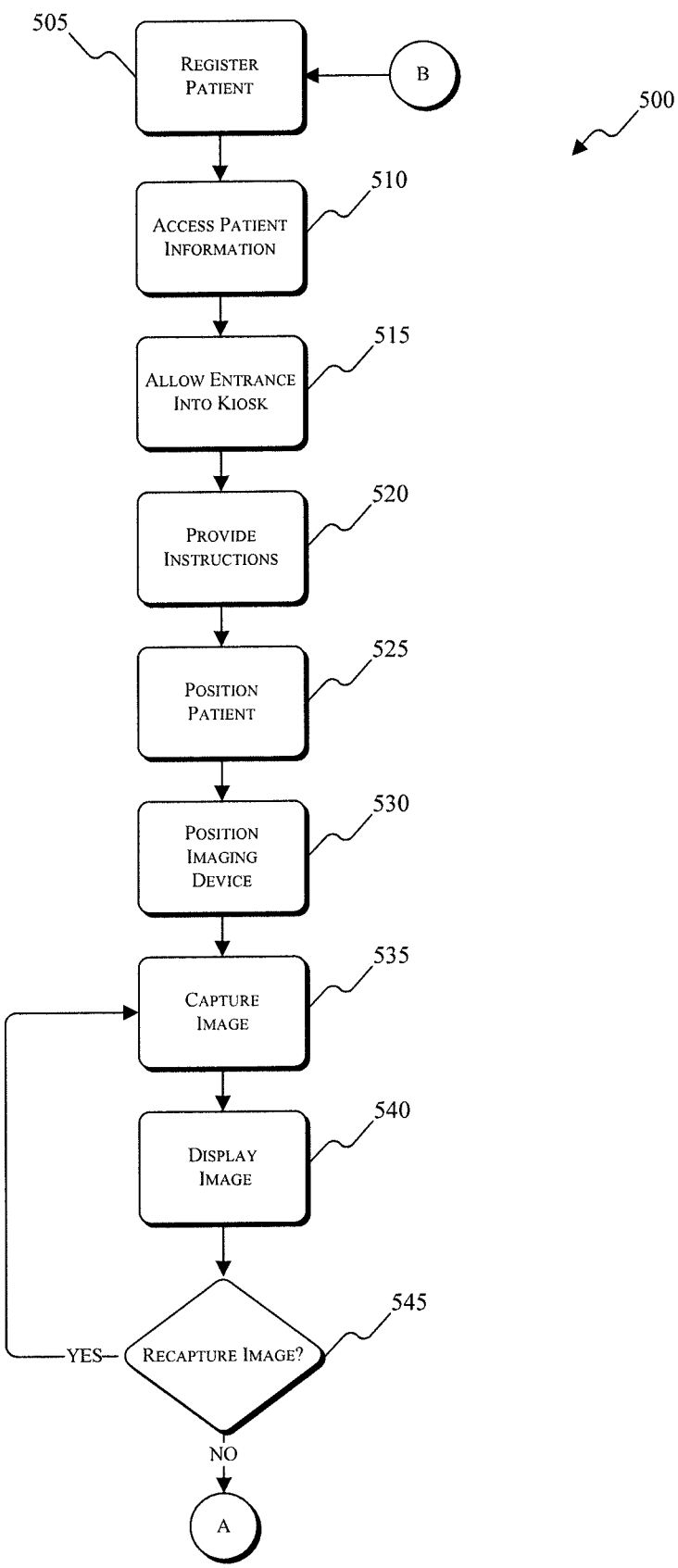
FIGS. 7-8 show a process for performing a diagnostic imaging procedure.
Figure 8:
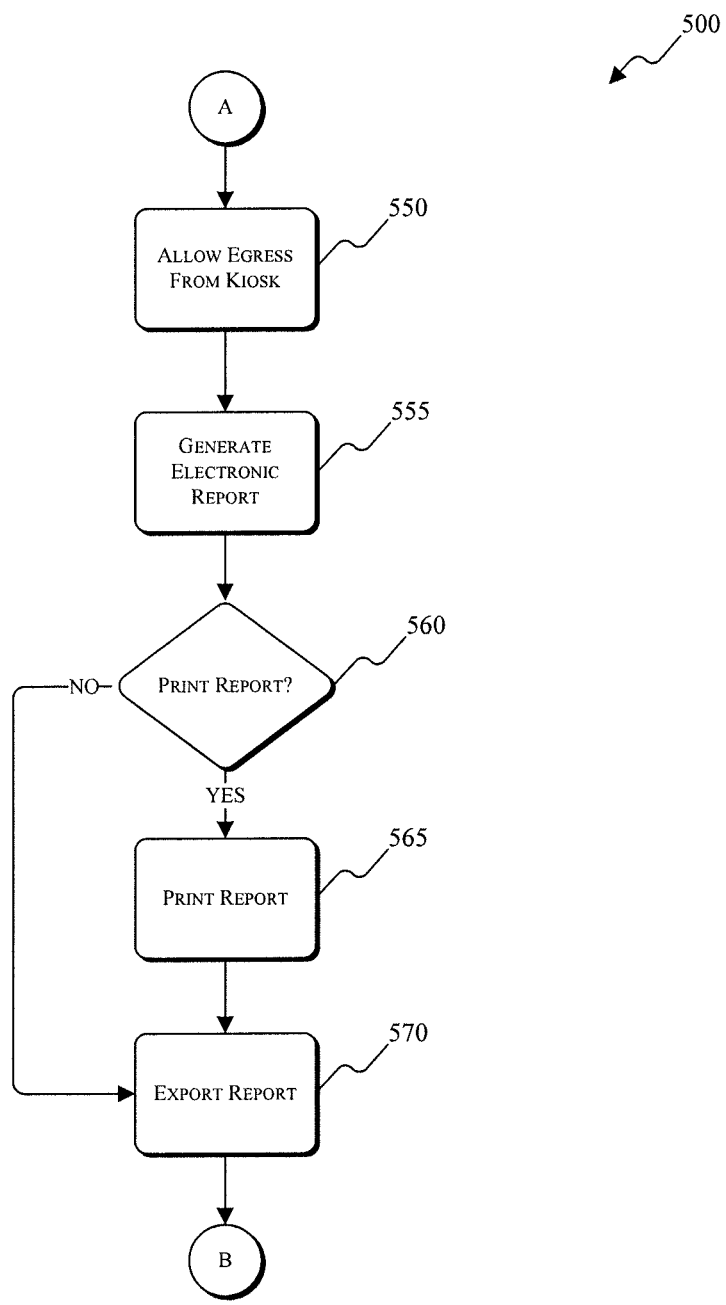

FIGS. 7 and 8 illustrate a process 500 for performing a diagnostic imaging procedure. Although the steps of the process 500 are illustrated in a particular order, various steps described herein with respect to the process 500 are capable of being executed simultaneously, in parallel, or in an order that differs from the illustrated serial manner of execution. At step 505, a patient is registered. The registration of a patient includes receiving a set of information from the patient, such as name, date of birth ("DOB"), payment information, personal health record information, and the like. For example, one or more virtual screens are presented to the user on an external user interface (e.g., the external display 320A). Using an input mechanism, the user selects or enters the information required to complete the registration process into one or more user input sections (e.g., text boxes, check boxes, etc.). For example, the user populates the user input sections by entering text via a mechanical or virtual keyboard of a computer or similar processing device, and using a pointing or selection device such as a mouse to control a cursor on the display 320A. Input signals from the keyboard and the mouse are received, processed, and translated into a visual result or action on the display 320A. For example, if the user enters text using a keyboard, the activated keys produce signals which are represented as type-written text on the external display 320A. Similarly, a mouse click, which corresponds to a location of the cursor on the screen, results in selecting/ deselecting a dropdown menu, the position of a fader, etc. In other implementations, the user input sections are accessed and controlled using a touch-screen device and a user's finger strokes or tapping are used to populate the input sections. In addition to manual entry and selections from a dropdown menu, the user input sections can be populated using a virtual or physical dial, fader, or the like.

After the patient registration information has been entered, a virtual or physical user identification mechanism is generated. For example, the user identification mechanism can be a password, a personal identification number ("PIN"), an account number, etc. that is able to be entered using the external display 320A during subsequent visits to a diagnostic imaging kiosk or similar device (e.g., another device connected to the diagnostic imaging kiosk via the same network, or connected to one or more of the same databases). Additionally or alternatively, the user identification mechanism is a physical user identification card that is printed and dispensed to the patient. If a patient has already received a user identification mechanism, the user identification mechanism can be used to forgo the registration process on subsequent visits.

The payment information includes, for example, a payment selection, such as credit card, on-line pay service, debit card, cash, check, credits, etc. In some embodiments, the cost of a diagnostic imaging procedure is displayed to the patient on the external display 320A. The patient is then able to allocate available funds to pay for the procedure or buy additional credits (e.g., using a credit card, cash, etc.). As described above, the kiosk 65 includes a variety of mechanisms for receiving payments (e.g., the magnetic stripe reader 240, the bill pay unit 250, etc.). Using these mechanisms, the patient is able to purchase additional credits with which to pay for a diagnostic imaging procedure. In some embodiments, an Internet or web-based on-line payment service (e.g., PayPal™) can also be used to pay for the diagnostic imaging procedure. Additionally or alternatively, the kiosk is also able to bill or invoice patients on a per-procedure basis, or a patient's financial information is linked to the user identification mechanism for automatic deductions or charges.

The costs associated with a diagnostic imaging procedure can be location and time specific. For example, a standard rate can be set based on a first location. Then, as the kiosk 65 is deployed to various locations, the costs associated with the diagnostic imaging procedure are adjusted based on current currency exchange rates (i.e., from one country to another country), based on state, local, or federal taxes, based on local costs for electricity, bandwidth, and the like, gross domestic product, average household income, insurance premiums, etc. In some embodiments, the kiosk 65 is capable of calculating the costs associated with the diagnostic imaging procedure. In other embodiments, the kiosk 65 receives the costs associated with a diagnostic imaging procedure from a remote location through a network. In some embodiments, credits for diagnostic imaging procedures can be purchased in advance of a procedure using a website or from a medical center. For example, a patient, or an individual acting on the patient's behalf, is able to access a website associated with the kiosk 65, register (as described above), and purchase credits for a diagnostic imaging procedure without having to be present at the kiosk 65. The patient is also able to schedule an appointment to use the kiosk 65 ahead of time. Such an appointment can be made using a website, from a medical center, at the kiosk 65, etc. If the costs associated with the diagnostic imaging procedure have changed or differ from when the credits were purchased, the patient is notified of the difference or change at the kiosk 65, via email, via text message, etc.

Because the kiosk 65 is capable of being deployed in remote locations, underdeveloped locations, disaster areas, or other areas where the costs of the diagnostic imaging procedure may be beyond the financial resources of a general population, donations can be made to fund the diagnostic procedures. For example, the website that allows a patient to purchase credits can also be configured to receive donations. The donations are location specific and allow individuals or organizations to contribute a lump sum that is then dispersed on a procedure-by-procedure basis. When a patient in such a location reaches the payment stage of the registration process, the donated credits are accessed and the patient is informed that the costs associated with the procedure have already been received.

Following step 505, the patient's information is accessed (step 510). The patient's information includes, for example, medical records, prior diagnostic images (e.g., X-rays), contact information, payment information, a photograph, etc., as described above. In some embodiments, the patient information is accessed by the kiosk 65 and provided to the remote technician when the patient is ready to begin a procedure (as described below). In other embodiments, once the patient has registered, the patient's identity is provided to a remote technician and the patient information is automatically retrieved from a database and displayed to the remote technician. The patient is then allowed to access or enter the kiosk 65 (step 515). The status of the kiosk 65 (e.g., occupied, door locked, etc.) is capable of being displayed on the external display 320A to indicate to the patient when the kiosk 65 is available to be entered, as described below. In some embodiments, the patient uses the user identification card and a magnetic stripe reader to unlock the door to the kiosk 65. In other embodiments (e.g., when the user identification mechanism is a PIN), the radiological technician remotely opens or unlocks the door to the kiosk 65. The door includes, for example, an electromagnetic lock. In some embodiments, a "master" or "supervisor" identification card allows a supervisor to access the kiosk 65 at any time.

Once inside the kiosk 65, the patient uses the user identification mechanism to alert a remote technician that they are ready to begin the procedure. As previously described, the patient's information can be provided to the remote technician following the use of the user identification mechanism. The patient is then presented with instructions related to the diagnostic imaging procedure (step 520). For example, the instructions that are presented are based on one or more diagnostic imaging procedure instruction signals received from the remote technician's workstation. The instructions are presented on an internal user interface (e.g., the internal display 315A). An avatar provides instructions related to, for example, the position of the patient (step 525). The avatar enables a consistent interactive user interface which can be programmed to provide instructions in any of a plurality of languages and dialects. The instructions are presented by an avatar representing the remote technician and include combinations of audio, pictures, video, and the like. For example, instructions include the remote technician providing voice instructions, an image of the position where the patient should be standing, and a video or animation of the patient moving into the correct position. The sounds, images, and videos that are displayed to the patient on the internal display 315A are controlled by the remote technician over the network. In some embodiments, the kiosk 65 includes footprints on the floor of the kiosk 65 to assist the patient in identifying the correct location to stand. The remote technician uses the first and second cameras to view the kiosk 65 and ensure that the patient is properly positioned. In some embodiments, the viewing directions of the first and second cameras are substantially orthogonal to one another to provide the remote technician with multiple vantage points from which to view the patient and ensure proper positioning.

After the patient has been properly positioned, the remote technician positions the imaging device (e.g., the X-ray unit 465 and the DR panel 435) (step 530). As described above, the X-ray unit 465 and the DR panel 435 are configured to move in synchronicity such that the X-ray unit 465 is always properly positioned with respect to the DR panel 435. Positioning the X-ray unit 465 also includes adjusting various settings of the imaging device, such as aperture size (e.g., collimator height and width) and exposure settings. In some embodiments, laser lines are used to assist the remote technician in properly adjusting the setting of the imaging device. When the patient is properly positioned, the imaging device is properly positioned, and the imaging device settings are correct, the diagnostic image is captured (step 535). The captured diagnostic image is then displayed on the internal display 315A and/or at the remote technician's workstation (step 540). The displayed diagnostic image is, for example, a lower resolution version of the full-resolution DICOM image. The remote technician is able to review the image and determine whether, for example, the image is of insufficient quality and if another diagnostic image needs to be captured (step 545). For example, the remote technician checks for patient motion during capture, checks for patient position during capture, and ensures that a proper dose was used during the exposure. If the diagnostic image is of insufficient quality, the process 500 returns to step 535 and a new diagnostic image is captured. Once a diagnostic image of sufficient quality has been captured, the process 500 proceeds to section A shown in and described with respect to FIG. 8.

Following step 545 and the completion of the diagnostic image capture, the patient is able to exit the kiosk 65 (step 550). For example, the remote technician opens the door or releases the door lock to allow the patient to exit the kiosk 65. In some embodiments, the door lock is configured such that, in the event of a failure of the door lock, the patient is able to open the door. An electronic report associated with the diagnostic imaging procedure is then generated (step 555). The report includes, for example, updated information for the patient's health record and/or medical records, a copy of or link to the captured diagnostic images, time and date information, payment information, and the like. If the user wishes to have the report printed (step 560), the report can be printed from the kiosk 65 (step 565). If the patient does not wish to have the report printed, or the report has already been printed, the report is exported (step 570) to, for example, a personal health record (e.g., Google Health, TELERAD, etc.), a storage device, or another similar database that is accessible through a network (e.g., the networks 15, 20, 25, or 30). Exporting the report can also include burning the report to a CD, copying the report to a portable flash drive (e.g., a USB mass storage device), and the like. The various physical and electronic reporting techniques allow the patient to track the results of their diagnostic imaging procedures and readily provide the results to a physician. The patient's history of procedures, medical history, and personal information can also be tracked via the user identification mechanism. Following the export of the report, the kiosk 65 is once again available for use and the process 500 proceeds to section B of FIG. 7 and step 505.

As previously described, the steps of the process 500 are capable of being executed simultaneously, in parallel, or in an order that differs from the illustrated serial manner of execution. For example, as one patient is in the kiosk 65 for a diagnostic imaging procedure, a second patient can be outside of the kiosk 65 registering for a procedure, printing a report, scheduling an appointment, etc. As such, although the process 500 is described with respect to a single patient, the kiosk 65 is configured to have multiple iterations of the process 500 being executed simultaneously. In some embodiments, the kiosk 65 is configured for additional diagnostic or general health related tests, such as taking blood pressure, taking temperature, measuring height, and measuring weight. Additionally or alternatively, tests or screenings such as cholesterol, body fat, and the like can also be performed.

The process 500 described above with respect to FIGS. 8 and 9 is facilitated, at least in part, by the interactions between the kiosk 65 (e.g., the internal and external user interfaces, the diagnostic imaging unit, the router, the controllers, etc.), the remote technician's workstation, and additional networked components (e.g., personal health records databases, PACS, etc.). The interactions between the remote technician's workstation and the kiosk 65 are achieved using a combination of hardware and software. For example, the kiosk 65 communicatively connects to the remote technician's workstation using hardware such as, among other things, the router 345 described above. The interactions between the remote technician's workstation and the kiosk 65 also include software that is stored in the kiosk 65, the technician's workstation, or on a server accessible using a network. The software is configured to generate a plurality of virtual interfaces or screens on, for example, the internal display 315A of the kiosk 65, the external display 320A of the kiosk 65, and at the remote technician's workstation (e.g., on one or more monitors).

The screens are presented to a patient or a remote technician to complete the execution of the diagnostic imaging procedure. In some embodiments of the invention, screens such as those illustrated in FIGS. 9-16 are generated. The screens can be divided into three categories: (1) external user interface screens; (2) internal user interface screens; and (3) remote technician screens. The internal and external user interface screens are described herein with respect to separate user interfaces. However, in some embodiments, the external user interface screens and the internal user interface screens are capable of being presented to a patient on a single user interface (e.g., the internal user interface).

Figure 9:
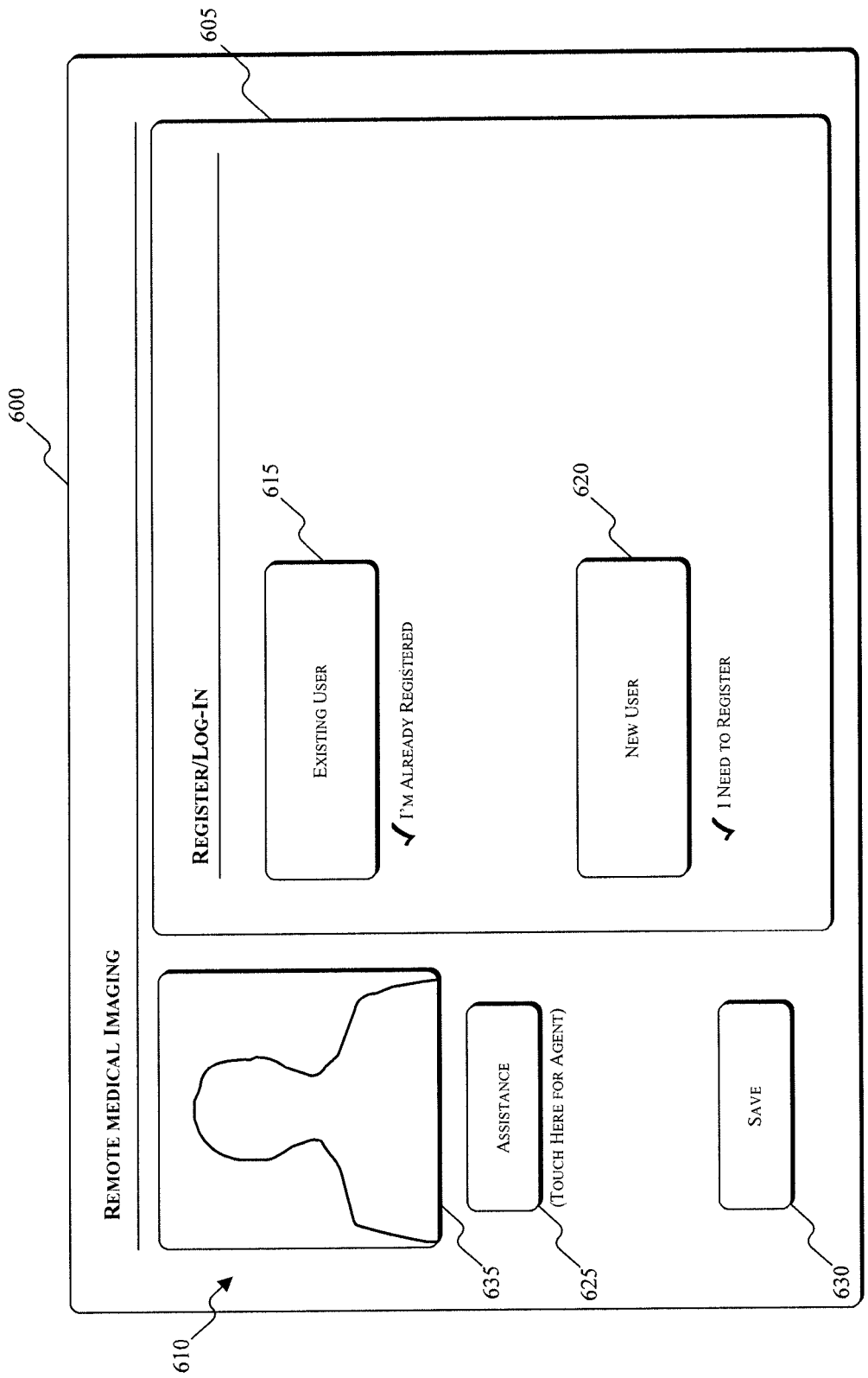
FIGS. 9-13 illustrate remote medical imaging user interface screens according to embodiments of the invention.

FIG. 9 illustrates a screen 600 configured to allow a patient to register or log-in to the system 10. For example, the screen 600 includes a first selection area 605 and a second selection area 610. The first selection area 605 includes an existing user button 615 and a new user button 620. If the patient has already completed the registration process and received a user identification mechanism (e.g., a password, a card, a PIN, etc.), the patient is able to forgo the registration process by selecting the existing user button 615 and using the previously provided user identification mechanism. If the user identification mechanism is a password, PIN, or the like, the patient is prompted to enter the user identification mechanism on the user interface. If the user identification mechanism is a physical card (e.g., including a magnetic stripe), the user is able to, for example, select the existing user button 615 and swipe the card in the magnetic stripe reader 240. In such an instance, the patient's information is automatically accessed without requiring further input from the patient. If the patient is using the diagnostic imaging kiosk 65 for the first time, the patient is able to initiate the registration process by selecting the new user button 620. The registration process is described in greater detail below.

The second selection area 610 includes an assistance button 625, a save button 630, and a portrait area 635. The assistance button 625 is selectable throughout the registration process and is configured to provide the patient with access to live assistance with, among other things, entering registration data, selecting payment options, and the like. The assistance button 625 connects the external user interface to a remote assistance service through a network (e.g., the networks 15, 20, 25, or 30). In some embodiments, the assistance button 625 connects the user interface to a remote technician. In other embodiments, the assistance button 625 connects the user interface to an assistance service other than a remote technician. The assistance service is, for example, a call center that specializes in the registration and remote diagnostic imaging process, but does not assist in taking the actual diagnostic image. Compartmentalizing the assistance service and the remote technicians allows the remote technicians to focus their time on capturing the diagnostic images and reduces the amount of time a patient waits to have the diagnostic image taken. The connection to the remote assistance service includes voice communication and video interaction. The video interaction includes, for example, an avatar of an assistance professional or the remote technician. After the assistance button 625 is selected and the user interface is connected to the assistance service, the assistance professional or the remote technician is able to remotely enter registration information, payment information, health record information, and the like based on information provided by the patient. Such a feature is beneficial in areas that may be undereducated, less technically savvy, or that have language barriers. The save button 630 allows the patient to save information that has been entered during the registration process, or changes that the patient has made to account parameters. In some embodiments, the save button 630 is persistent throughout the registration process or account update process.

If the patient selects the new user button 620, additional screens are presented to register the patient. For example, the registration process can be divided into four primary sections: (1) register; (2) payment; (3) personal health record; and (4) diagnostic image. These sections are shown in and described with respect to FIGS. 10-13. Additionally, although the screens illustrated in FIGS. 10-13 are described with respect to the registration process, existing users are able to log-in using a screen similar to that described below with respect to FIG. 10, or existing users are able to modify account parameters related to personal health records, payment options, and the like using screens similar to those shown in and described with respect to FIGS. 11-13.

Figure 10:
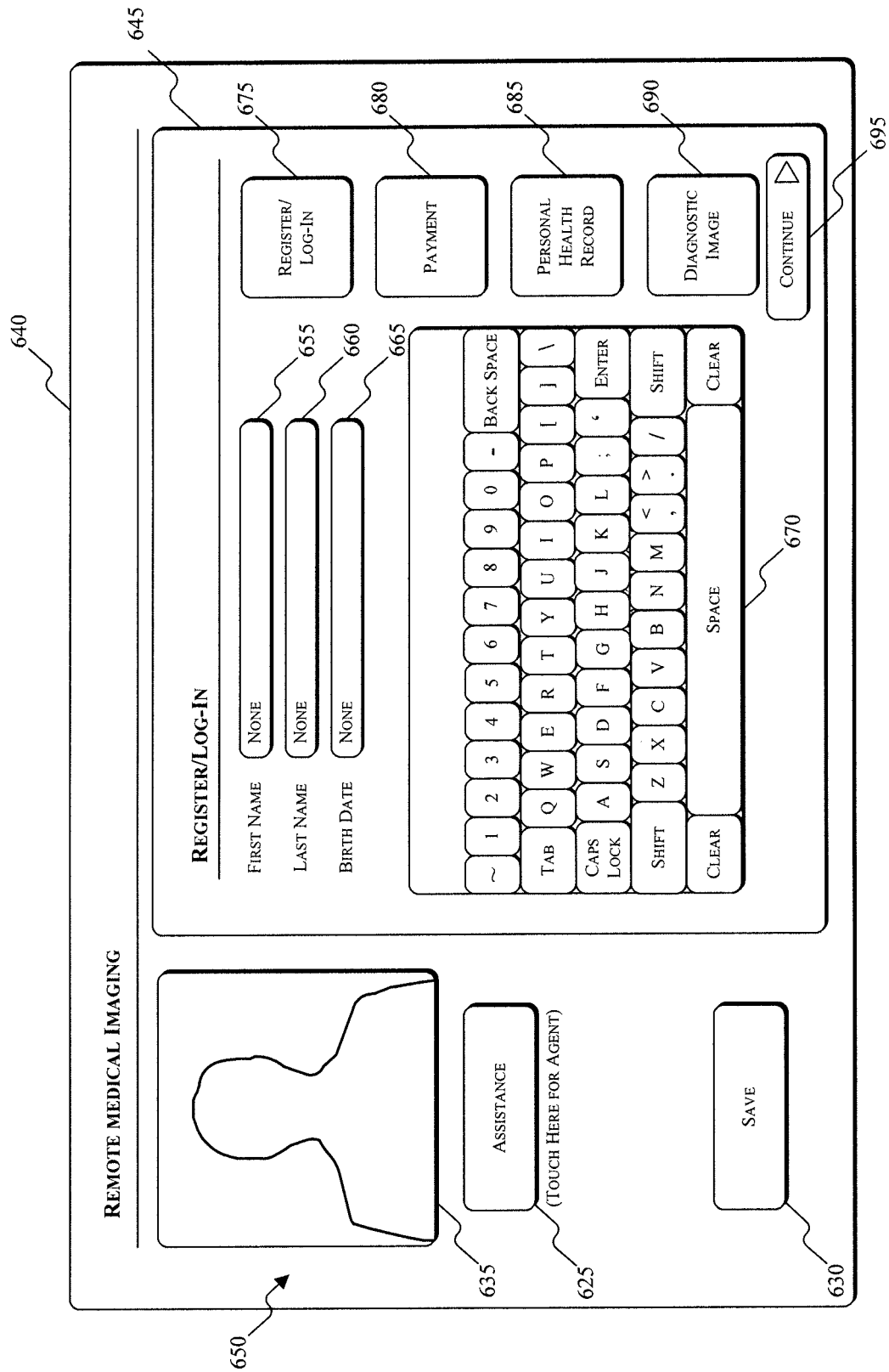

FIG. 10 illustrates a screen 640 for entering registration information. The screen 640 includes a first selection area 645 and a second selection area 650. The second selection area 650 is substantially similar to the second selection area 610 described above with respect to the screen 600. In the illustrated embodiment, the registration information is input into the first selection area 645 and includes the patient's first name, last name, and date of birth. The registration information is entered into corresponding input sections for the patient's first name 655, last name 660, and date of birth 665. The screen 640 also includes a virtual keyboard 670. The keyboard 670 is configured to allow the user to enter the registration information manually. In some embodiments, the keyboard is presented on a touch-screen interface as described above. In other embodiments, a physical keyboard, mouse, or similar user input device is used to enter the registration information. The first selection area 645 also includes a variety of navigation buttons that allow the patient to navigate through the registration process. For example, the navigation buttons include a register/log-in button 675, a payment button 680, a personal health record button 685, a diagnostic image button 690, and a continue button 695. The buttons 675-695 allow the patient to select or jump to a variety of different sections of the registration process. For example, if the patient wishes to modify or select a personal health record preference before entering payment information, the patient selects the personal health record button 685. If the patient prefers to serially step through the registration process, the continue button 695 allows the user to enter or view information consecutively in each of the sections of the registration process.

Figure 11:
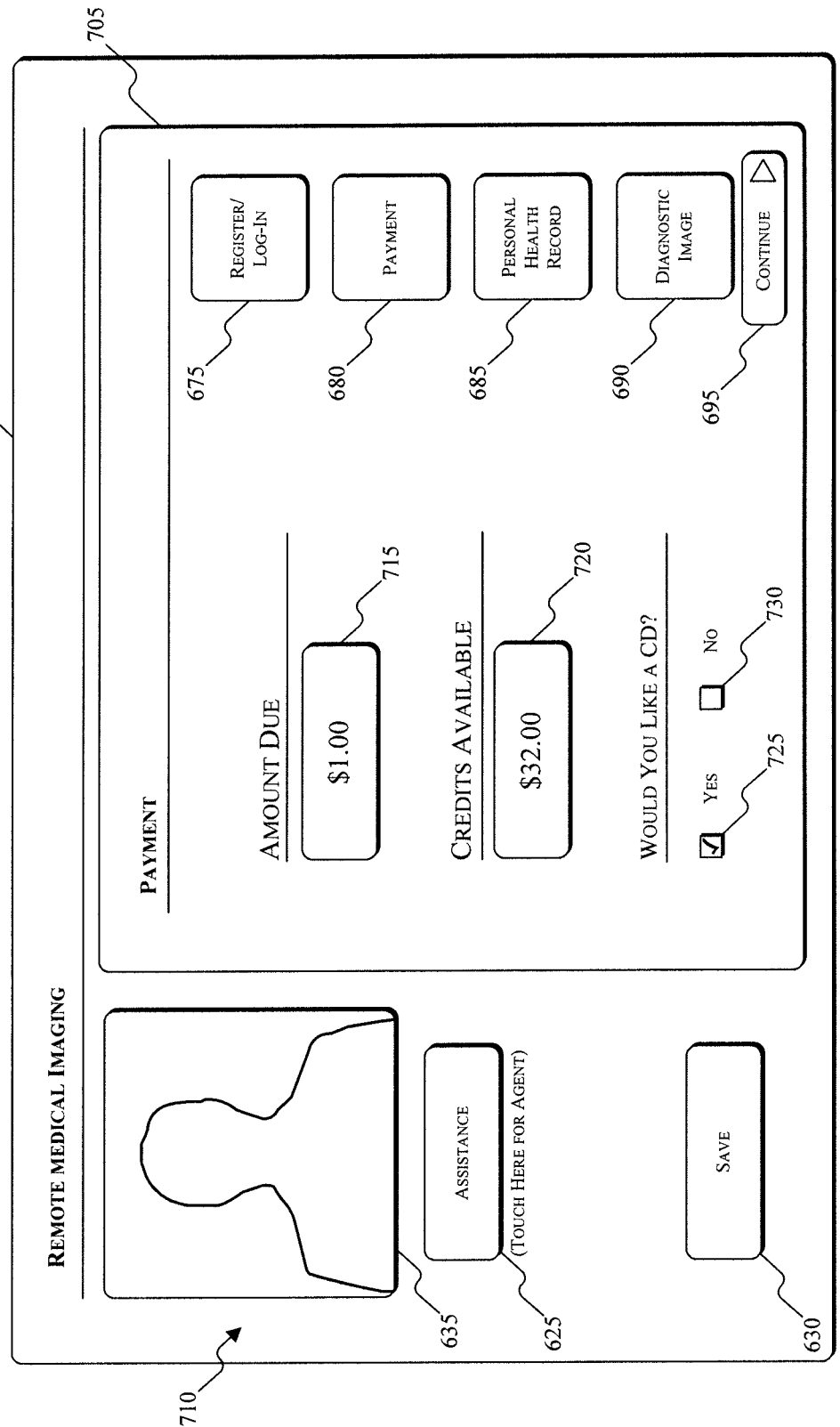

FIG. 11 illustrates a payment screen 700 for selecting payment options and is similar to the screen 640 described above. The screen 700 includes a first selection area 705 and a second selection area 710. The second selection area 710 is substantially similar to the selection area 610 described above with respect to FIG. 9. Also, the first selection area 705 includes navigation buttons 675-695, as described above. The first selection area 705 also includes an amount due area 715, a credits available area 720, and a CD selection area for indicating whether the patient would like a diagnostic image to be burned to a CD. The CD selection area includes a 'YES' checkbox 725 and a 'NO' checkbox 730 that can be selected using the touch-screen display, a mouse, or another similar user input device, as described above. The amount due area 715 displays the cost of the diagnostic imaging procedure to the patient. The cost is illustrated as $1.00, but the cost of the diagnostic imaging procedure is set based on, among other things, a variety of location dependent factors, as described above. The credits available area 720 indicates how many credits the patient has available to pay for the diagnostic imaging procedure. In some embodiments, the credits available area 720 is a button. In such embodiments, by selecting the credits available button 720, the patient is prompted with a variety of payment options. For example, the patient is able to select cash, credit card, check, etc. as a payment method with which to purchase additional credits. In some embodiments, the patient is not able to advance past the payment screen 700 until enough credits have been purchased to pay for the diagnostic imaging procedure. In some embodiments, when the patient has enough credits available to pay for the diagnostic imaging procedure, the credits are automatically deducted from the patient's account following the completion of the diagnostic imaging procedure. In other embodiments, the patient is able to manually deduct credits from their account by selecting the amount due area 715. In such embodiments, the amount due area 715 is configured as a button or similar input device.

Figure 12:
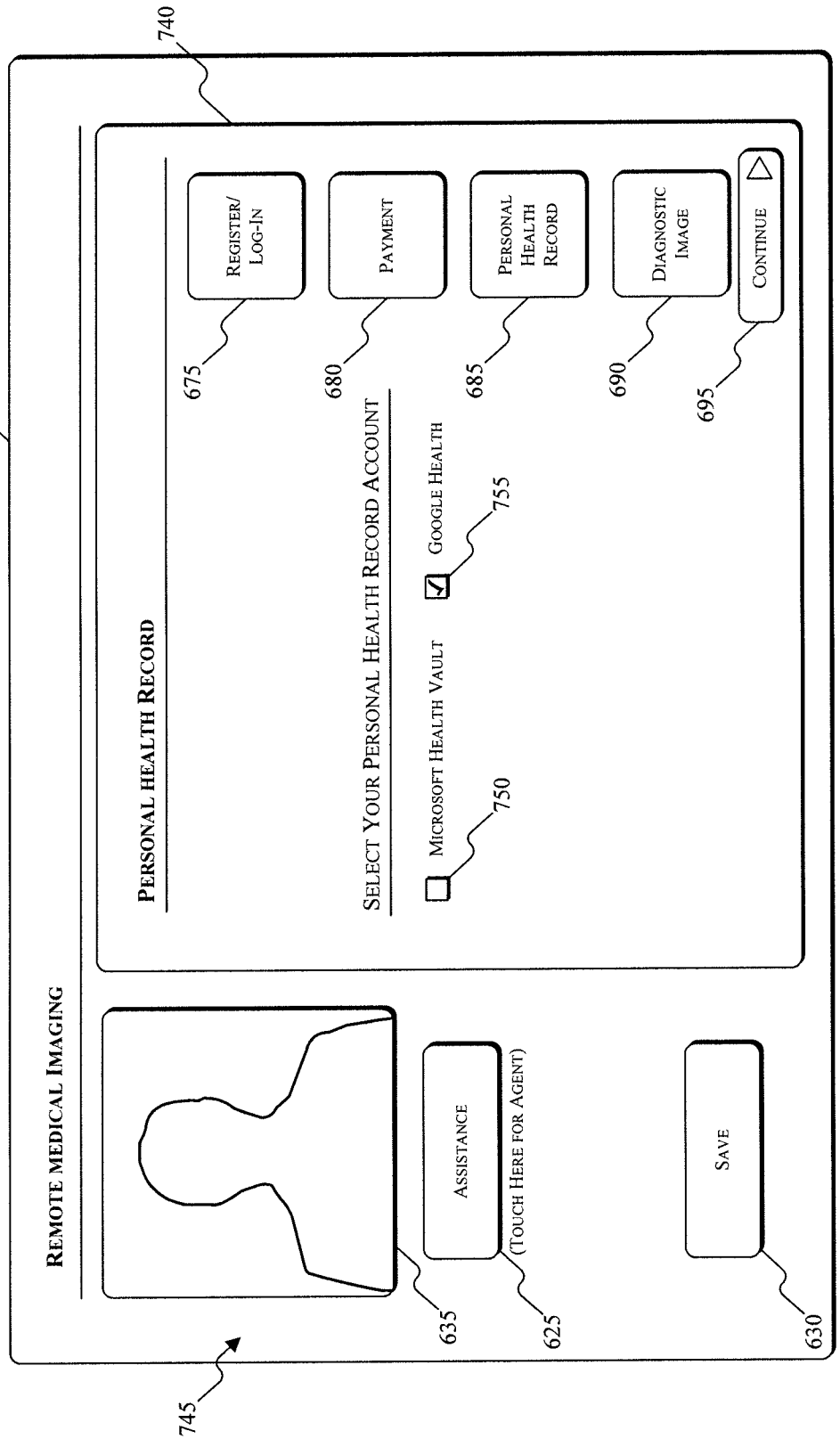

FIG. 12 illustrates a personal health record screen 735 for selecting a personal health record. The screen 735 includes a first selection area 740 and a second selection area 745. The second selection area 740 is similar to the selection area 610 described above with respect to FIG. 9. The first selection area 740 includes navigation buttons 675-695, as described above. The first selection area 740 also includes a variety of personal health record selection options. For example, in the illustrated embodiment, the patient is able to select a Microsoft Health Vault account using a corresponding checkbox 750, or a Google Health account using a corresponding checkbox 755. In some embodiments, if the patient does not already have a personal health record account set up, a personal health record account is automatically set up based on previously entered registration information. Additionally or alternatively, the patient is able to select a different personal health record by entering, for example, a URL corresponding to a web-based health record service other than Microsoft Health Vault and Google Health.

Figure 13:
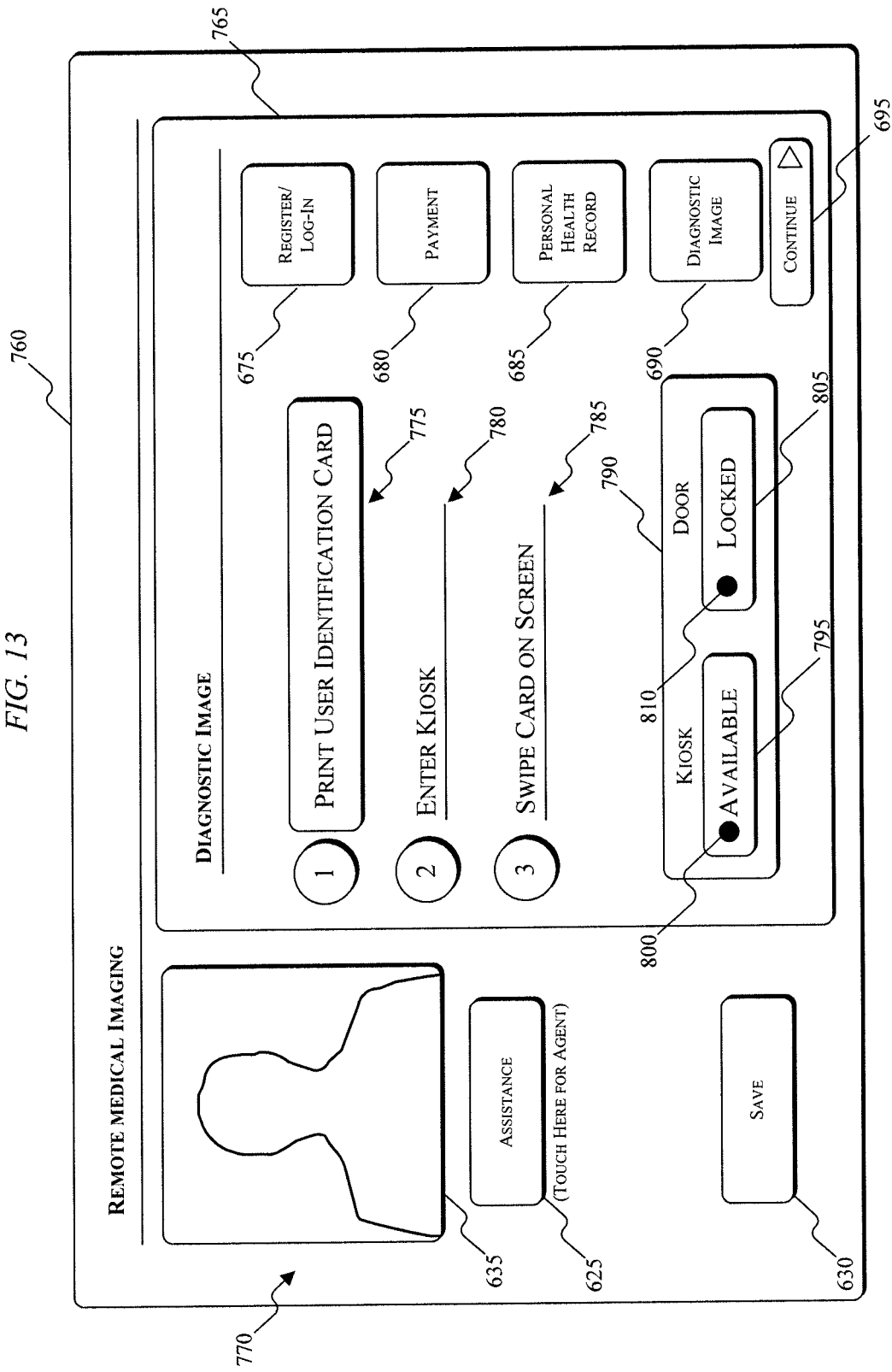

FIG. 13 illustrates a diagnostic image screen 760. The screen 760 includes a first selection area 765 and a second selection area 770. The second selection area 770 is similar to the selection area 610 described above with respect to FIG. 9, and the first selection area 765 includes navigation buttons 675-695 as described above. The first selection area 765 also includes a set of instructions for completing the registration process. For example, in the illustrated embodiment, the set of steps include instructions for printing a user identification card 775, instructions to enter the kiosk 780, and instructions to swipe the card on or near the internal user interface 785. In the illustrated embodiment, the instructions for printing the user identification card include a corresponding button which, when selected, causes the user identification card to be printed. In other embodiments, a password or PIN number is generated in addition to or in place of the user identification card. The first selection area 765 also includes a status area 790. The status area 790 includes a status indicator for each of the kiosk 65 and the kiosk door. For example, a kiosk status indicator 795 includes a light 800 and corresponding text that indicates whether the kiosk 65 is available for entry. In some embodiments, the light 800 is illuminated green when the kiosk 65 is available and red when the kiosk 65 is not available. The text included in the kiosk status indicator is modified to match the light 800 by indicating that the booth is available (e.g., when the light 800 is green) and not available (e.g. when the light 800 is red). Similarly, the kiosk door status indicator 805 includes a light 810 and corresponding text that indicates whether the kiosk door is locked or unlocked. In some embodiments, the light 810 is illuminated green when the kiosk door is unlocked and red when the kiosk door is locked. When the kiosk 65 is both available and the door is unlocked, the patient is able to enter the kiosk 65.

After the patient has completed the registration or log-in process described above with respect to FIGS. 9-13, the patient is able to enter the kiosk 65. Upon entering the kiosk 65, the patient is greeted by the internal display 315A which requests that the patient swipe the user identification card using a magnetic stripe reader located within the kiosk 65. Additionally or alternatively, the user enters a password or PIN to initiate the diagnostic imaging procedure. As described above, after the patient has initiated the diagnostic imaging procedure, a call is placed to a remote technician, the patient's records are accessed, and two-way communication between the kiosk 65 and the remote technician's workstation is initiated. The kiosk 65 calls a call center that includes, for example, a plurality of remote technicians. However, the number of kiosks in use often exceeds the number of available remote technicians. As such, the kiosk 65 may be placed in a queue of kiosks that are ready for diagnostic imaging procedures to be executed. When a remote technician becomes available, two-way communication between the kiosk 65 and the available remote technician's workstation is initiated.

Figure 14:
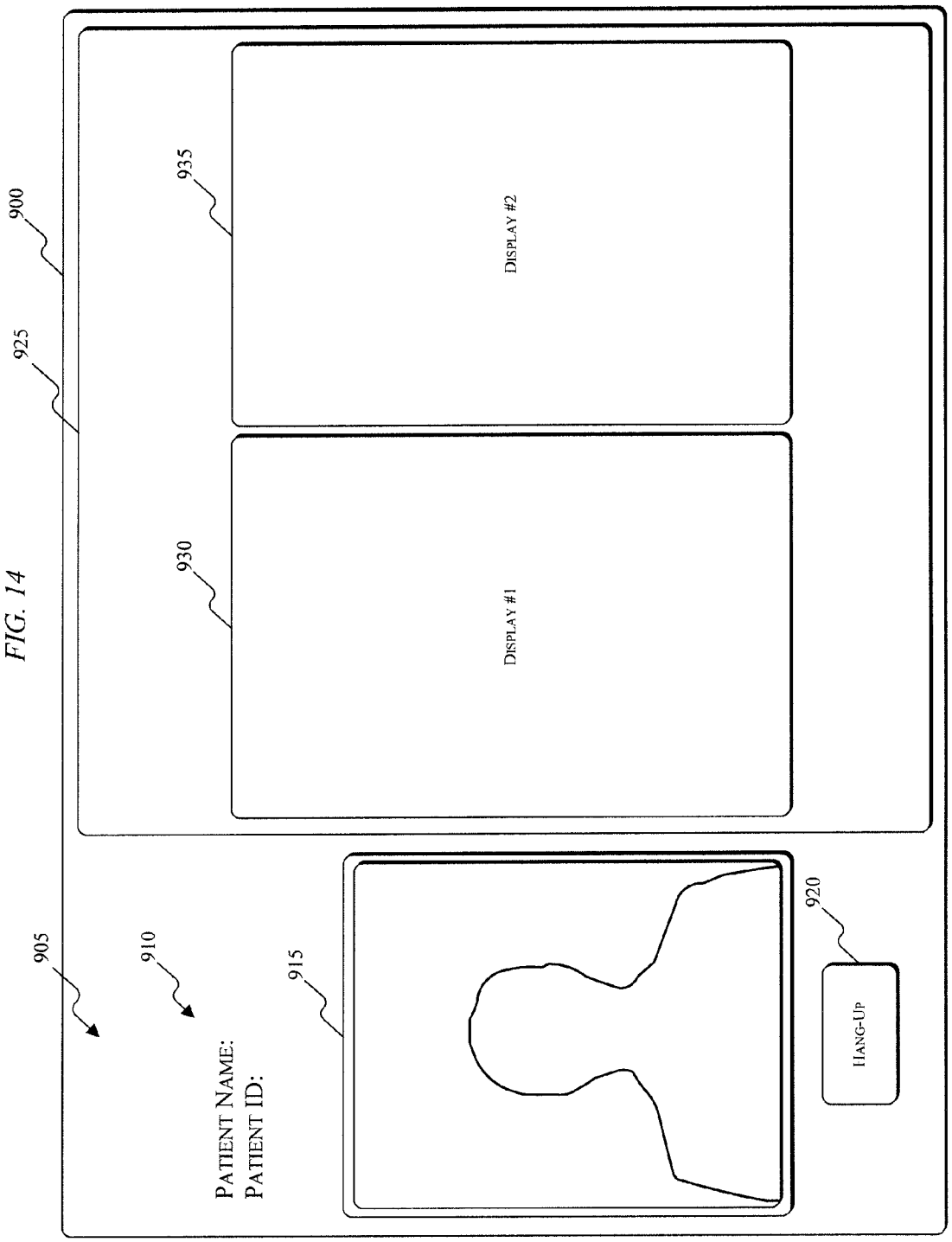
FIG. 14 illustrates a remote medical imaging user interface screen according to another embodiment of the invention.

Upon initiating the diagnostic imaging procedure, the patient is presented with a screen on the internal user interface such as screen 900 illustrated in FIG. 14. The screen 900 includes two primary display areas. A first display area 905 includes patient information 910 (e.g., patient name, patient identification number, etc.), a display of the remote technician's avatar 915, and a hang-up button 920. The hang-up button 920 allows the user to end the two-way communication with the remote technician (e.g., following the completion of a diagnostic imaging procedure). In some embodiments, the hang-up button 920 is disabled to prevent the patient from prematurely ending communication with the remote technician. If communication between the kiosk 65 and the remote technician's workstation is prematurely ended (i.e., prior to completing the diagnostic imaging procedure), the kiosk 65 is configured to, for example, disable the diagnostic imaging unit until communication between the kiosk 65 and the remote technician's workstation is re-established. The patient is able to re-establish communication with the remote technician's workstation by re-swiping the user identification card or re-entering the password, PIN, or the like.

A second display area 925 includes a first display section 930 and a second display section 935. The first and second display sections 930 and 935 are configured to display combinations of images, animations, videos, and the like to the patient. For example, the remote technician is able to control the items being displayed in the first display section 930 and the second display section 935 remotely from their workstation (e.g., by generating corresponding signals that are transmitted through a packet-switched network). The information presented to the patient in the first and second display sections 930 and 935 includes instructions for being properly positioned with respect to the diagnostic imaging unit, removing jewelry, and the like. The instructions can be presented to the patient using images, videos, animations, or combinations thereof. The remote technician is also able to provide voice-over instructions to the patient or to play pre-recorded instructions associated with each step of the diagnostic imaging procedure. In other embodiments, the second display area includes a single display section.

In addition to displaying instructions to the patient, the first and second display sections 930 and 935 can also be used to display the results of the diagnostic imaging procedure. For example, following the capture of a diagnostic image, the full-resolution diagnostic image or a reduced-resolution version of the diagnostic image is displayed in one of the first and second display sections 930 and 935. The display of the diagnostic image is controlled by the remote technician (e.g., by generating and transmitting corresponding signals). For example, the remote technician first views the captured diagnostic image to ensure that the image is of sufficient quality. If the image is of sufficient quality, the remote technician selects an option to display the image to the patient on the internal user interface. In some embodiments, the remote technician is able to display multiple diagnostic images to the patient. For example, the remote technician is able to display a diagnostic image captured during the current diagnostic imaging procedure (i.e., stored in the PACS 340), as well as a diagnostic image from a previous diagnostic imaging procedure. The image from the previous procedure is retrieved from, for example, the PACS 55 connected to the first local network 25. The two images can then be displayed side-by-side to illustrate, for example, changes in the patient's condition.

Figure 15:
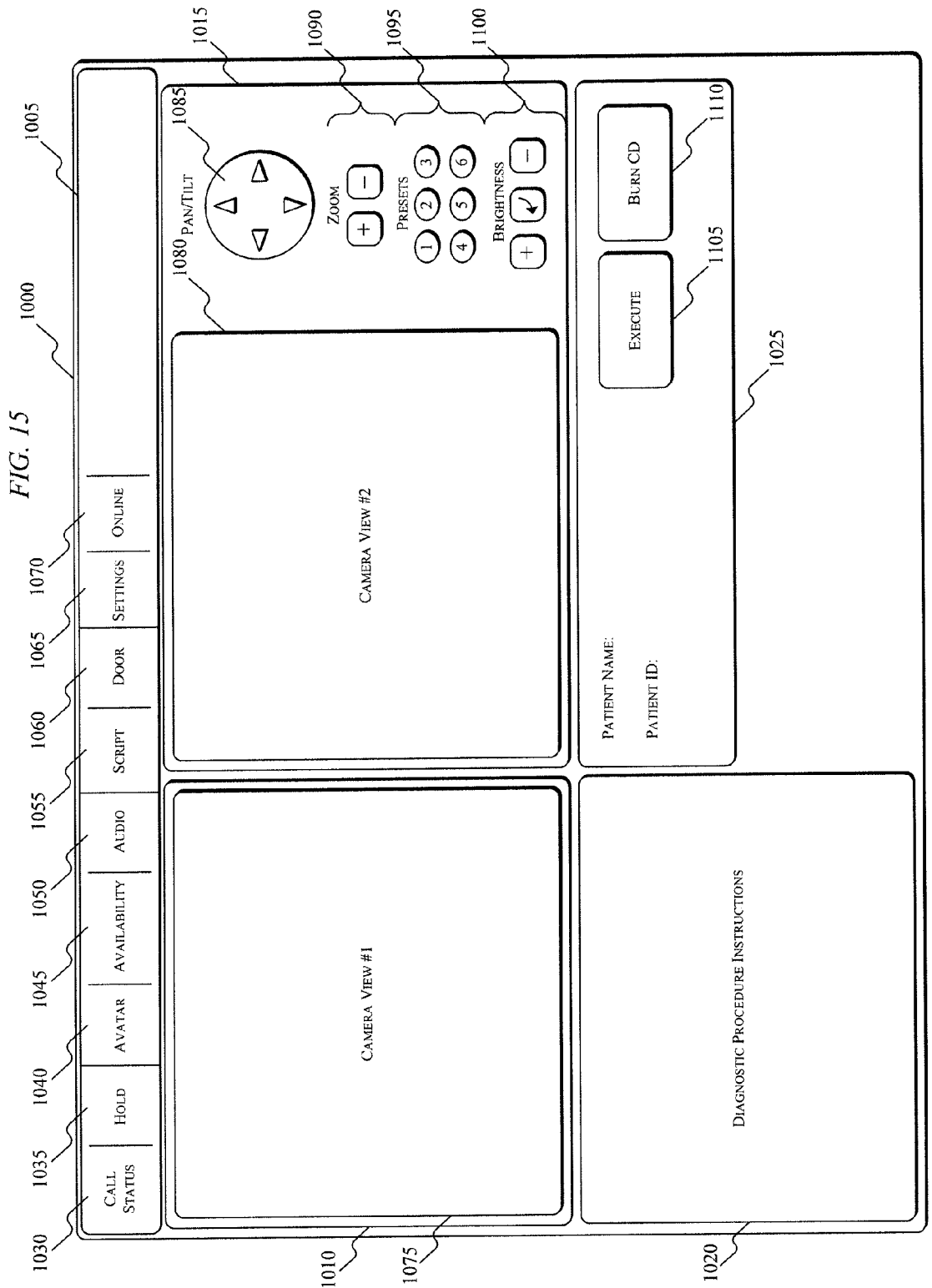
FIG. 15 illustrates a remote technician workstation screen according to an embodiment of the invention.

As previously described, the diagnostic imaging kiosk 65 is controlled through a network from the remote technician's workstation. When connected to the diagnostic imaging kiosk 65, the remote technician is presented with a plurality of screens which are used to control the kiosk 65. For example, FIG. 15 illustrates a screen 1000 for controlling the kiosk 65. The screen includes a status bar 1005, a first camera display area 1010, a second camera display area 1015, a diagnostic procedure instructions area 1020, and a session control section 1025. The status bar 1005 includes a variety of buttons which provide the remote technician with the current status of the workstation, as well as the ability to modify the status of the workstation. For example, the status bar 1005 includes a call status portion 1030, a hold portion 1035, an avatar portion 1040, an availability portion 1045, an audio portion 1050, a script portion 1055, a door portion 1060, a settings portion 1065, and an online portion 1070. The call status portion 1030 provides an indication to the remote technician that there is currently an active call with the kiosk 65 or that there is not an active call with the kiosk 65. In some embodiments, the call status portion 1030 is configured as a button that allows the remote technician to answer a call from a kiosk 65, end a call from a kiosk 65, or switch from a call with one kiosk to a call with another kiosk. The hold portion 1035 includes, for example, a button that allows the remote technician to place a current call on hold.

The avatar portion 1040 allows the remote technician to select, among other things, an avatar to be displayed (e.g., male or female) on the internal or external user interfaces of the kiosk 65 and whether the avatar is to be displayed. The avatar portion 1040 also provides an indication to the remote technician of which avatar is being displayed. The availability portion 1045 allows the remote technician to select whether their workstation is available to connect to a kiosk, and provides an indication of such to the remote technician. For example, when the remote technician's workspace is available, the workstation is placed in a queue of workstations to await a call from a kiosk. The audio portion 1050 allows the remote technician to control various audio settings of the workstation (e.g., volume, etc.). The script portion 1055 allows the remote technician to select any of a variety of prepared scripts related to diagnostic imaging procedures. For example, the scripts can be specific to a type of diagnostic image (e.g., X-ray), a particular language, or the like. The door portion 1060 allows the remote technician to control whether the door lock on a kiosk's door is in a locked state or an unlocked state, as well as provide an indication of the current state of the kiosk's door. The settings portion 1065 allows the remote technician to select one or more settings related to the operation of the workstation or the control of the kiosk. For example, the settings include a language setting, a default camera setting, a default avatar setting, etc. The online portion 1070 provides an indication to the remote technician related to whether the technician's workstation is currently online or offline. The online portion 1070 also allows the remote technician to select whether the workstation is online or offline. In other embodiments, the screen 1000 includes additional or different portions in the status bar 1005.

The first camera display area 1010 includes a first camera view 1075. The first camera view 1075 provides a display to the remote technician of a first kiosk video feed. In the illustrated embodiment, the first camera view is associated with a fixed camera (i.e., a camera that cannot be rotated or otherwise moved by the remote technician. The second camera display area 1015 includes a second camera view 1080 and a set of camera controls. The second camera view 1080 provides a display to the remote technician of a second kiosk video feed. The set of camera controls are used to control the display of the second kiosk video feed. For example, the camera controls include a camera panning section 1085 that allows the remote technician to adjust the direction the second camera is pointed (e.g., up, down, left, right, etc.). The camera controls also include zoom controls 1090 (e.g., zoom in and zoom out), preset camera views 1095 (e.g., preset to show different portions of the kiosk), and brightness controls 1100 (e.g., brightness up, brightness down, brightness reset, etc.).

The diagnostic procedure instructions area 1020 displays the set of instructions associated with a particular diagnostic imaging procedure. For example, depending on the script selected in the script portion 1055 of the status bar 1005, a corresponding set of instructions are displayed in the diagnostic procedure instructions area 1020. The remote technician is able to manually select each step of the procedure (e.g., by double-clicking) to display corresponding images, video, and animations to the patient, as well as provide corresponding voice instructions to the patient. The remote technician can verify that the patient has completed an instruction by monitoring the first and second camera views 1075 and 1080.

The session control section 1025 extends the functionality of the status bar 1005. For example, the session control section 1025 provides the remote technician with an indication of the patient's name and identification, as well as the ability to execute the diagnostic image capture (e.g., using an execute button 1105) and burn a CD that includes that diagnostic image (e.g., using a burn CD button 1110). In some embodiments, the screen 1000 is configured to allow the remote technician to annotate a diagnostic image. For example, the remote technician is able to add text, arrows, shapes, voice dictation, etc. to highlight areas of interest in the diagnostic image. In some embodiments, the annotations are then displayed to the patient on the internal user interface 315A. The remote technician is also able to, for example, control a cursor on the internal user interface 315A or annotate a diagnostic image while the diagnostic image is being displayed on the internal user interface 315A.

Figure 16:
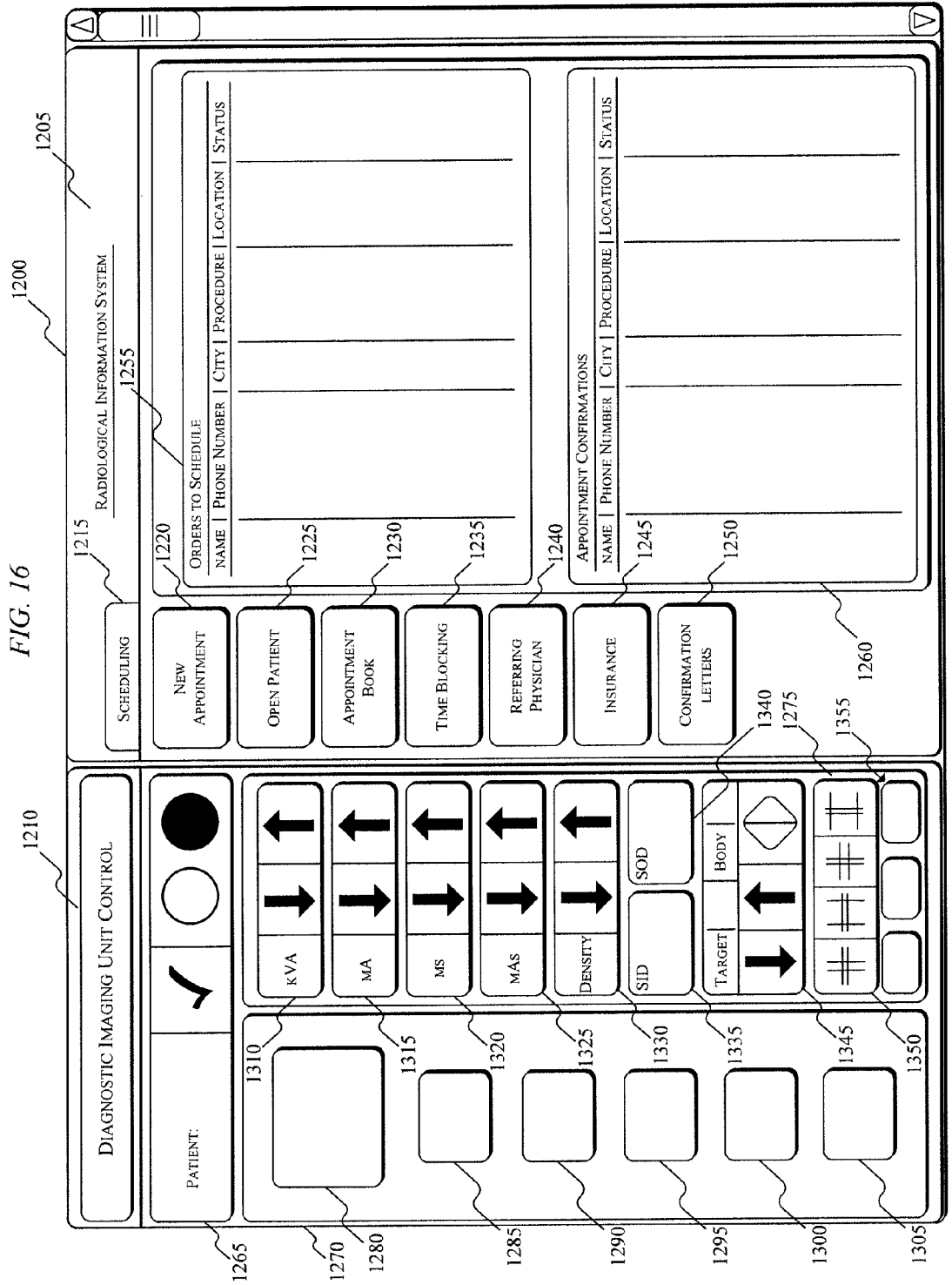
FIG. 16 illustrates a remote technician workstation screen according to another embodiment of the invention.

In addition to the screen 1000 described above, the remote technician's workstation also includes a screen 1200 as illustrated in FIG. 16. The screen 1200 is configured to control various settings of the diagnostic imaging unit, as well as provide information to the remote technician related to the current patient in the kiosk, scheduled patients, patient information, insurance information, and the like (e.g., by generating and transmitting corresponding control signals). For example, the screen 1200 includes an information management section 1205 and a diagnostic imaging unit control section 1210. The information management section 1205 is connected to, for example, one or more information management systems, one or more personal health record systems, and one or more additional databases. In the illustrated embodiment of the information management section 1205, a single tab portion is illustrated that corresponds to a scheduling tab 1215. Additional tabs can also be included in the information management section to streamline workflow and data management. The scheduling tab 1215 includes a new appointment button 1220, an open patient button 1225, an appointment book button 1230, a time blocking button 1235, a referring physician button 1240, an insurance button 1245, and a confirmation letters button 1250. In the illustrated embodiment, the appointment book is shown which includes an orders-to-schedule table 1255 and an appointments confirmation table 1260. The appointment book is configured to provide the remote technician with information related to each patient that has scheduled a diagnostic imaging procedure or is currently undergoing a diagnostic imaging procedure.

The new appointment button 1220 is configured to allow the remote technician to schedule a new appointment for a patient. The open patient button 1225 is configured to allow the remote technician to access a specific patient's records or information. The appointment book button 1230 is configured to allow the remote technician to review scheduled diagnostic procedures for one or more kiosks, the patient's information, and the like. The time blocking button 1235 is configured to allow the remote technician to block off portions of time when appointments can or cannot be scheduled, when the remote technician is or is not available, when the kiosk is or is not available, and the like. The referring physician button 1240 is configured to allow the remote technician to access a patient's physicians' information, contact the referring physician, refer the patient to a physician, or the like. The insurance button 1245 is configured to allow the remote technician to access a patient's insurance information to, for example, confirm that the patient has insurance or that the patient's insurance covers a particular procedure. The confirmation letters button 1250 is configured to allow the remote technician to access a library of pre-formatted letters. The letters can include, for example, the results of a diagnostic test, a patient referral, etc. In some embodiments, additional buttons are included to streamline the workflow of the remote technician.

The diagnostic imaging unit control section 1210 includes, among other things, a status bar 1265, a preset procedure section 1270, and a manual control section 1275. The status bar 1265 includes, for example, a patient's name, one or more error codes associated with the diagnostic imaging unit and an indication of whether the diagnostic image can be taken (e.g., based on current settings of the diagnostic imaging unit). The preset procedure section 1270 includes image portions 1280-1305 that correspond to various types of diagnostic images that can be taken. For example, the image portions 1280-1305 correspond to X-ray procedures for various portions of the human body (e.g., chest, skull, spine, complete skeletal, abdominal, etc.). By selecting one of the image portions 1280-1305, the settings for the diagnostic imaging unit (described below) are automatically adjusted to preset values.

The remote technician is also able to manually control the settings for the diagnostic imaging unit. For example, with respect to an X-ray device, the manual control section 1275 includes manual up/down controls for the X-ray tube voltage 1310, the X-ray tube current 1315, the X-ray exposure time 1320, the milliampere-seconds 1325, and density 1330. The manual control section 1275 also includes an indication of the source-detector distance ("SID") 1335 and the source-object distance ("SOD") 1340. The remote technician is able to adjust the height of the diagnostic imaging unit using a height adjustment section 1345. The height adjustment section also includes a display of the target height and a body height. After the remote technician has properly adjusted the height of the diagnostic imaging unit, the remote technician is able to adjust the width and height of a collimator of the diagnostic imaging unit. For example, a collimator adjustment portion 1350 is used to adjust a height and width of a visible area of light that corresponds to an area to be imaged. In the illustrated embodiment, the manual control section 1275 also includes a plurality of additional buttons 1355 for selecting or controlling additional features of the diagnostic imaging kiosk.

Thus, the invention provides, among other things, systems and method for performing remote diagnostic imaging. Various features and advantages of the invention are set forth in the following claims.

What is claimed is:

1. A diagnostic imaging system comprising:
   a remote diagnostic imaging station including a diagnostic imaging device, a communications interface, and a user interface, the remote diagnostic imaging station configured to be connected to a packet-switched network; and
   a diagnostic imaging control station separate from the remote diagnostic imaging station and communicatively connected to the remote diagnostic imaging station through the packet-switched network, the diagnostic imaging control station configured to
   generate a position control signal, the position control signal associated with a physical position of at least a portion of the diagnostic imaging device,
   transmit the position control signal through the packet-switched network to the remote diagnostic imaging station,
   generate a diagnostic imaging procedure instruction signal, the diagnostic imaging procedure instruction signal instructing a patient located at the remote diagnostic imaging station to change position,
   transmit the diagnostic imaging procedure instruction signal through the packet-switched network to the remote diagnostic imaging station,
   generate a diagnostic imaging capture signal, the diagnostic imaging capture signal operable to initiate capture of a diagnostic image,
   transmit the diagnostic imaging capture signal through the packet-switched network to the remote diagnostic imaging station, and
   display the captured diagnostic image.

2. The diagnostic imaging system of claim 1, wherein the remote diagnostic imaging station further includes a surveillance device that is configured to be controlled remotely by the diagnostic imaging control station, the surveillance device also configured to transmit at least one of a video signal and an audio signal through the packet-switched network.

3. The diagnostic imaging system of claim 1, wherein the remote diagnostic imaging station is further configured to store the captured diagnostic image on a local picture archiving and communication system ("PACS") within the remote diagnostic imaging station.

4. The diagnostic imaging system of claim 3, wherein the remote diagnostic imaging station is further configured to transmit the captured diagnostic image from the local PACS to a remote PACS that is connected to the remote diagnostic imaging station through the packet-switched network.

5. The diagnostic imaging system of claim 1, wherein the remote diagnostic imaging station is further configured to provide patient instructions related to a diagnostic imaging procedure, the patient instructions based on the diagnostic imaging procedure instruction signal received through the packet-switched network from the diagnostic imaging control station.

6. A method of performing a diagnostic imaging procedure, the method comprising:
   connecting to a remote diagnostic imaging station through a packet-switched network;
   generating a position control signal, the position control signal associated with a physical position of at least a portion of a diagnostic imaging device;
   transmitting the position control signal through the packet-switched network to the remote diagnostic imaging station;
   generating a diagnostic imaging procedure instruction signal, the diagnostic imaging procedure instruction signal instructing a patient located at the remote diagnostic imaging station to change position;
   transmitting the diagnostic imaging procedure instruction signal through the packet-switched network to the remote diagnostic imaging station,
   generating a diagnostic imaging capture signal, the diagnostic imaging capture signal operable to initiate capture of a diagnostic image;
   transmitting the diagnostic imaging capture signal through the packet-switched network to the remote diagnostic imaging station; and
   displaying the captured diagnostic image.

7. The method of claim 6, further comprising receiving at least one of a surveillance video signal and a surveillance audio signal through the packet-switched network.

8. The method of claim 6, wherein generating the diagnostic imaging procedure instruction signal includes generating at least one of audio instructions and visual instructions for instructing the patient located at the remote diagnostic imaging station to change position.

9. The method of claim 6, wherein generating the position control signal includes generating a signal associated with a physical position of at least a portion of an X-ray device.

10. The method of claim 9, wherein generating the signal associated with the physical position of at least a portion of the X-ray device includes generating a signal operable to adjust a height of the X-ray device.

\* \* \* \* \*